United States Patent
Corsello et al.

(10) Patent No.: US 12,313,632 B2
(45) Date of Patent: May 27, 2025

(54) TEPOXALIN TARGETING OF ABCB1 OVEREXPRESSING CANCERS

(71) Applicants: THE BROAD INSTITUTE, INC., Cambridge, MA (US); DANA-FARBER CANCER INSTITUTE, INC.; INSTITUTO CARLOS SLIM DE LA SALUD, A.C., Mexico City (MX)

(72) Inventors: Steven Corsello, Boston, MA (US); Ryan Spangler, Cambridge, MA (US); Rohith Nagari, Cambridge, MA (US); Todd Golub, Cambridge, MA (US)

(73) Assignees: THE BROAD INSTITUTE, INC., Cambridge, MA (US); DANA-FARBER CANCER INSTITUTE, INC., Boston, MA (US); INSTITUTO CARLOS SLIM DE LA SALUD, A.C., Mexico City (MX)

( * ) Notice: Subject to any disclaimer, the term of this patent is extended or adjusted under 35 U.S.C. 154(b) by 1053 days.

(21) Appl. No.: 17/291,458

(22) PCT Filed: Nov. 8, 2019

(86) PCT No.: PCT/US2019/060516
§ 371 (c)(1),
(2) Date: May 5, 2021

(87) PCT Pub. No.: WO2020/097492
PCT Pub. Date: May 14, 2020

(65) Prior Publication Data
US 2022/0065864 A1    Mar. 3, 2022

Related U.S. Application Data

(60) Provisional application No. 62/758,294, filed on Nov. 9, 2018.

(51) Int. Cl.
*C12Q 1/68* (2018.01)
*A61K 31/415* (2006.01)
(Continued)

(52) U.S. Cl.
CPC ..... *G01N 33/57492* (2013.01); *A61K 31/415* (2013.01); *A61K 45/06* (2013.01);
(Continued)

(58) Field of Classification Search
None
See application file for complete search history.

(56) References Cited

U.S. PATENT DOCUMENTS

2010/0196907 A1    8/2010    Semizarov et al.

OTHER PUBLICATIONS

Lee (Immunology Letters, vol. 53, pp. 109-113, 1996). (Year: 1996).*

(Continued)

*Primary Examiner* — Jeanine A Goldberg
(74) *Attorney, Agent, or Firm* — Day Pitney LLP; Christopher R. Cowles; Erica A. Fishel

(57) ABSTRACT

The present disclosure relates to compositions and methods for the diagnosis and treatment or prevention of cancers that exhibit elevated expression and/or amplification of the ABCB1 (MDR1) transporter, optionally for reasons related to development of chemotherapeutic resistance having occurred during treatment with an initial chemotherapeutic drug. In particular, the instant disclosure provides for identification of a cancer as possessing elevated ABCB1 expression and/or exhibiting resistance to a non-tepoxalin chemotherapeutic drug, and selecting and/or administering tepoxalin, a tepoxalin derivative and/or metabolite thereof as a therapeutic agent for such a cancer and/or subject having or at risk of developing such a cancer. Methods and compositions for therapies that combine such tepoxalin or tepo- (Continued)

xalin-related compounds with other cancer therapies and/or chemotherapeutic agents are also provided.

15 Claims, 17 Drawing Sheets

Specification includes a Sequence Listing.

(51) Int. Cl.
*A61K 45/06* (2006.01)
*A61P 35/00* (2006.01)
*C07H 21/04* (2006.01)
*C12Q 1/6886* (2018.01)
*G01N 33/574* (2006.01)

(52) U.S. Cl.
CPC ............ *A61P 35/00* (2018.01); *C12Q 1/6886* (2013.01); *C12Q 2600/106* (2013.01); *C12Q 2600/158* (2013.01); *G01N 2333/70596* (2013.01)

(56) References Cited

OTHER PUBLICATIONS

Seubwai et al. (Oncology Research, vol. 23, pp. 21-28, 2016) (Year: 2016).*

International Search Report dated Apr. 14, 2020 for related Application No. PCT/US2019/060516.

Seubwai et al., Inhibition of NF-κB Activity Enhances Sensitivity to Anticancer Drugs in Cholangiocarcinoma Cells, Oncology Research, 2016, vol. 23, pp. 21-28; abstract; p. 24, col. 1, para 4; p. 26, col. 1, para 1.

Sottnik, The Role of Innate Immunity and Angiogenesis in Osteosarcoma Growth and Metastasis, Graduate Degree Program Paper, Colorado University, Spring 2010 [online]. [Retrieved on Jan. 21, 2020], Retrieved from the internet <URL: https:/lmountainscholar. orglbitstreamlhandle/10217/39051/Sottnik_colostate_0053A_10036. pdf ? sequence=1&isAllowed=y >; p. 149, para 3.

Reed K et al, "The temporal relationship between ABCB1 promoter hypomethylation, ABCB1 expression and acquisition of drug resistance", The Pharmacogenomics Journal, Nature Publishing Group, 2010.

Loftus J. P. et al, "The 5-lipoxygenase inhibitor tepoxalin induces oxidative damage and altered PTEN status prior to apoptosis in canine osteosarcoma cell lines: 5-lipoxygenase inhibition in osteosarcoma", Veterinary and Comparative Oncology, 2014.

Wakshlag Joseph J. et al, "5-Lipoxygenase expression and tepoxalin-induced cell death in squamous cell carcinomas in cats", American Journal of Veterinary Research, 2011.

* cited by examiner

| Cell line | ABCB1 log2 RNAseq TPM | PRISM IC50 (M) |
|---|---:|---:|
| COLO668_LUNG | 4.75 | 4.67E-07 |
| LS1034_LARGE_INTESTINE | 6.41 | 1.19E-06 |
| CADOES1_BONE | 4.37 | 1.49E-06 |
| HCC1588_LUNG | 5.05 | 1.62E-06 |
| OVTOKO_OVARY | 4.29 | 1.90E-06 |
| RCC10RGB_KIDNEY | 5.55 | 2.15E-06 |
| HCT15_LARGE_INTESTINE | 5.99 | 2.81E-06 |
| JHH7_LIVER | 4.71 | 2.85E-06 |
| LS513_LARGE_INTESTINE | 5.09 | 3.39E-06 |
| SNU1079_BILIARY_TRACT | 4.05 | 4.08E-06 |
| BEN_LUNG | 4.70 | 6.32E-06 |
| TT_THYROID | 5.69 | 6.57E-06 |
| VMRCRCW_KIDNEY | 4.74 | 8.85E-06 |
| SNUC4_LARGE_INTESTINE | 5.00 | 9.66E-06 |
| HT55_LARGE_INTESTINE | 4.21 | 9.96E-06 |

FIG. 3

| | |
|---|---|
| AAGCTGGAGAGATCCTCACC AAGCGGCTCCGATACAT | SEQ ID NO: 3 |
| aagctggagagatcctcac- aagcggctccgatacat | SEQ ID NO: 4 & 5 |
| aagctggagagatcctcaccaagcggctccgatacat | SEQ ID NO: 6 |
| aag------------------- ---cggctccgatacat | SEQ ID NO: 7 |
| aagctggagagatcctca-- -agcggctccgatacat | SEQ ID NO: 8 & 9 |
| aagctggagagatcctcacc a-gcggctccgatacat | SEQ ID NO: 10 & 11 |
| aagctggagagatcc------ -------------gatacat | SEQ ID NO: 12 |
| aagctggagagatcctcacc aagcggctccgatacat | SEQ ID NO: 13 |
| aagctgga-------------- ---cggctccgatacat | SEQ ID NO: 14 & 15 |
| aagctggagagatcctc----- -------cgatacat | SEQ ID NO: 16 |
| aagctggagagatc-------- -----------------at | SEQ ID NO: 20 |
| aagctggagagatcc------ aagcggctccgatacat | SEQ ID NO: 17 & 18 |
| aagctggagagat--------- -------------acat | SEQ ID NO: 19 |

FIG. 6A

| Drug | IC50 (absolute) |
|---|---|
| Paclitaxel | 165 nM |
| Tepoxalin | 7.8 uM |
| Elacridar | 1.9 uM |
| Valspodar | > 10 uM |
| Zosuquidar | > 10 uM |
| Tariquidar | > 10 uM |
| Dofequidar | > 10 uM |

FIG. 7B

| Drug | REC1 | LS1034 | LS1034-sg GFP | LS1034-sg ABCB1-2 |
|---|---|---|---|---|
| Paclitaxel | 14 nM | 165 nM | 375 nM | 570 nM |
| Tepoxalin | 1.4 uM | 7.8 uM | 9.5 uM | > 10 uM |
| Elacridar | 2.9 uM | 1.9 uM | 2.6 uM | 3.1 uM |
| Valspodar | 2.9 uM | > 10 uM | > 10 uM | > 10 uM |
| Zosuquidar | 6.3 uM | > 10 uM | > 10 uM | > 10 uM |
| Tariquidar | > 10 uM | > 10 uM | > 10 uM | > 10 uM |
| Dofequidar | > 10 uM | > 10 uM | > 10 uM | > 10 uM |

FIG. 8

SEQUENCE LISTING

<160> NUMBER OF SEQ ID NOS: 20

<210> SEQ ID NO 1
<211> LENGTH: 4363
<212> TYPE: DNA
<213> ORGANISM: Homo sapiens

<400> SEQUENCE: 1

```
gctcattcga gtagcggctc ttccaagctc aaagaagcag aggccgctgt tcgtttcctt      60
taggtctttc cactaaagtc ggagtatctt cttccaaaat ttcacgtctt ggtggccgtt     120
ccaaggagcg cgaggtcgga atggatcttg aaggggaccg caatggagga gcaaagaaga     180
agaacttttt taaactgaac aataaaagtg aaaaagataa gaaggaaaag aaaccaactg     240
tcagtgtatt ttcaatgttt cgctattcaa attggcttga caagttgtat atggtggtgg     300
gaactttggc tgccatcatc catggggctg acttcctctc atgatgctg gtgtttggag      360 aaatgacaga tatctttgca aatgcaggaa atttagaaga tctgatgtca aacatcacta     420
atagaagtga tatcaatgat acagggttct tcatgaatct ggaggaagac atgaccaggt     480
atgcctatta ttacagtgga attggtgctg gggtgctggt gctgcttac attcaggttt      540 cattttggtg cctggcagct ggaagacaaa tacacaaaat tagaaaacag tttttttcatg    600 ctataatgcg acaggagata ggctggtttg atgtgcacga tgttggggag cttaacaccc     660
gacttacaga tgatgtctcc aagattaatg aaggaattgg tgacaaaatt ggaatgttct     720
ttcagtcaat ggcaacattt ttcactgggt ttatagtagg atttacacgt ggttggaagc     780 taaccttgt gattttggcc atcagtcctg ttcttggact gtcagctgct gtctgggcaa      840
agatactatc ttcatttact gataaagaac tcttagcgta tgcaaaagct ggagcagtag     900
ctgaagaggt cttggcagca attagaactg tgattgcatt tggaggacaa agaaaagaac     960
ttgaaaggta caacaaaaat ttagaagaag ctaaaagaat tgggataaag aaagctatta    1020
cagccaatat ttctataggt gctgctttcc tgctgatcta tgcatcttat gctctggcct    1080
tctggtatgg gaccaccttg gtcctctcag gggaatattc tattggacaa gtactcactg    1140
tattcttttc tgtattaatt ggggctttta gtgttggaca ggcatctcca agcattgaag    1200
catttgcaaa tgcaagagga gcagcttatg aaatcttcaa gataattgat aataagccaa    1260
gtattgacag ctattcgaag agtgggcaca accagataa tattaaggga aatttggaat    1320
tcagaaatgt tcacttcagt tacccatctc gaaaagaagt taagatcttg aagggtctga    1380
acctgaaggt gcagagtggg cagacggtgg ccctggttgg aaacagtggc tgtgggaaga    1440
gcacaacagt ccagctgatg cagaggctct atgaccccac agagggatg gtcagtgttg     1500 atggacagga tattaggacc ataaatgtaa ggtttctacg ggaaatcatt ggtgtggtga    1560
gtcaggaacc tgtattgttt gccaccacga tagctgaaaa cattcgctat ggccgtgaaa    1620
atgtcaccat ggatgagatt gagaaagctg tcaaggaagc caatgcctat gactttatca    1680
tgaaactgcc tcataaattt gacaccctgg ttggagagag aggggcccag ttgagtggtg    1740
ggcagaagca gaggatcgcc attgcacgtg ccctggttcg caacccaag atcctcctgc      1800 tggatgaggc cacgtcagcc ttggacacag aaagcgaagc agtggttcag gtggctctgg    1860
```

-continued

```
ataaggccag aaaaggtcgg accaccattg tgatagctca tcgtttgtct acagttcgta    1920
atgctgacgt catcgctggt ttcgatgatg gagtcattgt ggagaaagga aatcatgatg    1980
aactcatgaa agagaaaggc atttacttca aacttgtcac aatgcagaca gcaggaaatg    2040
aagttgaatt agaaaatgca gctgatgaat ccaaaagtga aattgatgcc ttggaaatgt    2100
cttcaaatga ttcaagatcc agtctaataa gaaaaagatc aactcgtagg agtgtccgtg    2160
gatcacaagc ccaagacaga aagcttagta ccaaagaggc tctggatgaa agtataccctc   2220 cagtttcctt ttggaggatt atgaagctaa atttaactga atggccttat tttgttgttg    2280
gtgtattttg tgccattata aatggaggcc tgcaaccagc atttgcaata atattttcaa    2340
agattatagg ggttttttaca agaattgatg atcctgaaac aaaacgacag aatagtaact   2400
tgttttcact attgtttcta gcccttggaa ttatttcttt tattacattt ttccttcagg    2460
gtttcacatt tggcaaagct ggagagatcc tcaccaagcg gctccgatac atggttttcc    2520
gatccatgct cagacaggat gtgagttggt ttgatgaccc taaaaacacc actggagcat    2580
tgactaccag gctcgccaat gatgctgctc aagttaaagg ggctataggt tccaggcttg    2640
ctgtaattac ccagaatata gcaaatcttg ggacaggaat aattatatcc ttcatctatg    2700
gttggcaact aacactgtta ctcttagcaa ttgtacccat cattgcaata gcaggagttg    2760
ttgaaatgaa aatgttgtct ggacaagcac tgaaagataa gaaagaacta gaaggttctg    2820
ggaagatcgc tactgaagca atagaaaact tccgaaccgt tgtttctttg actcaggagc    2880
agaagtttga acatatgtat gctcagagtt tgcaggtacc atacagaaac tctttgagga    2940
aagcacacat ctttggaatt acattttcct tcacccaggc aatgatgtat ttttcctatg    3000
ctggatgttt ccggtttgga gcctacttgg tggcacataa actcatgagc tttgaggatg    3060
ttctgttagt attttcagct gttgtctttg gtgccatggc cgtggggcaa gtcagttcat    3120
ttgctcctga ctatgccaaa gccaaaatat cagcagccca catcatcatg atcattgaaa    3180 aaacccttt gattgacagc tacagcacgg aaggcctaat gccgaacaca ttggaaggaa    3240
atgtcacatt tggtgaagtt gtattcaact atcccacccg accggacatc ccagtgcttc    3300
agggactgag cctggaggtg aagaagggcc agacgctggc tctggtgggc agcagtggct    3360
gtgggaagag cacagtggtc cagctcctgg agcggttcta cgacccctttg gcagggaaag    3420 tgctgcttga tggcaaagaa ataaagcgac tgaatgttca gtggctccga gcacacctgg    3480
gcatcgtgtc ccaggagccc atcctgtttg actgcagcat tgctgagaac attgcctatg    3540
gagacaacag ccgggtggtg tcacaggaag agattgtgag ggcagcaaag gaggccaaca    3600
tacatgcctt catcgagtca ctgcctaata aatatagcac taaagtagga gacaaaggaa    3660
ctcagctctc tggtggccag aaacaacgca ttgccatagc tcgtgccctt gttagacagc    3720
ctcatatttt gcttttggat gaagccacgt cagctctgga tacagaaagt gaaaaggttg    3780
tccaagaagc cctggacaaa gccagagaag gccgcacctg cattgtgatt gctcaccgcc    3840
tgtccaccat ccagaatgca gacttaatag tggtgtttca gaatggcaga gtcaaggagc    3900
atggcacgca tcagcagctg ctggcacaga aaggcatcta tttttcaatg gtcagtgtcc    3960
aggctggaac aaaagcgccag tgaactctga ctgtatgaga tgttaaatac ttttaatat    4020 ttgtttagat atgacattta ttcaaagtta aaagcaaaca cttacagaat tatgaagagg    4080
tatctgttta acatttcctc agtcaagttc agagtcttca gagacttcgt aattaaagga    4140
acagagtgag agacatcatc aagtggagag aaatcatagt ttaaactgca ttataaattt    4200
tataacagaa ttaaagtaga ttttaaaaga taaaatgtgt aattttgttt atattttccc    4260
```

```
atttggactg taactgactg ccttgctaaa agattataga agtagcaaaa agtattgaaa    4320
tgtttgcata aagtgtctat aataaaacta aactttcatg tga                      4363
```

<210> SEQ ID NO 2
<211> LENGTH: 1280
<212> TYPE: PRT
<213> ORGANISM: Homo sapiens

<400> SEQUENCE: 2

```
Met Asp Leu Glu Gly Asp Arg Asn Gly Gly Ala Lys Lys Asn Phe
1               5                   10                  15

Phe Lys Leu Asn Asn Lys Ser Glu Lys Asp Lys Lys Glu Lys Lys Pro
                20                  25                  30

Thr Val Ser Val Phe Ser Met Phe Arg Tyr Ser Asn Trp Leu Asp Lys
            35                  40                  45

Leu Tyr Met Val Val Gly Thr Leu Ala Ala Ile Ile His Gly Ala Gly
        50                  55                  60

Leu Pro Leu Met Met Leu Val Phe Gly Glu Met Thr Asp Ile Phe Ala
65                  70                  75                  80

Asn Ala Gly Asn Leu Glu Asp Leu Met Ser Asn Ile Thr Asn Arg Ser
                85                  90                  95

Asp Ile Asn Asp Thr Gly Phe Phe Met Asn Leu Glu Glu Asp Met Thr
            100                 105                 110

Arg Tyr Ala Tyr Tyr Tyr Ser Gly Ile Gly Ala Gly Val Leu Val Ala
        115                 120                 125

Ala Tyr Ile Gln Val Ser Phe Trp Cys Leu Ala Ala Gly Arg Gln Ile
    130                 135                 140

His Lys Ile Arg Lys Gln Phe Phe His Ala Ile Met Arg Gln Glu Ile
145                 150                 155                 160

Gly Trp Phe Asp Val His Asp Val Gly Glu Leu Asn Thr Arg Leu Thr
                165                 170                 175

Asp Asp Val Ser Lys Ile Asn Glu Gly Ile Gly Asp Lys Ile Gly Met
            180                 185                 190

Phe Phe Gln Ser Met Ala Thr Phe Phe Thr Gly Phe Ile Val Gly Phe
        195                 200                 205

Thr Arg Gly Trp Lys Leu Thr Leu Val Ile Leu Ala Ile Ser Pro Val
    210                 215                 220

Leu Gly Leu Ser Ala Ala Val Trp Ala Lys Ile Leu Ser Ser Phe Thr
225                 230                 235                 240

Asp Lys Glu Leu Leu Ala Tyr Ala Lys Ala Gly Ala Val Ala Glu Glu
                245                 250                 255

Val Leu Ala Ala Ile Arg Thr Val Ile Ala Phe Gly Gly Gln Lys Lys
            260                 265                 270

Glu Leu Glu Arg Tyr Asn Lys Asn Leu Glu Glu Ala Lys Arg Ile Gly
        275                 280                 285

Ile Lys Lys Ala Ile Thr Ala Asn Ile Ser Ile Gly Ala Ala Phe Leu
    290                 295                 300

Leu Ile Tyr Ala Ser Tyr Ala Leu Ala Phe Trp Tyr Gly Thr Thr Leu
305                 310                 315                 320

Val Leu Ser Gly Glu Tyr Ser Ile Gly Gln Val Leu Thr Val Phe Phe
                325                 330                 335

Ser Val Leu Ile Gly Ala Phe Ser Val Gly Gln Ala Ser Pro Ser Ile
            340                 345                 350
```

-continued

Glu Ala Phe Ala Asn Ala Arg Gly Ala Ala Tyr Glu Ile Phe Lys Ile
            355                 360                 365

Ile Asp Asn Lys Pro Ser Ile Asp Ser Tyr Ser Lys Ser Gly His Lys
    370                 375                 380

Pro Asp Asn Ile Lys Gly Asn Leu Glu Phe Arg Asn Val His Phe Ser
385                 390                 395                 400

Tyr Pro Ser Arg Lys Glu Val Lys Ile Leu Lys Gly Leu Asn Leu Lys
                405                 410                 415

Val Gln Ser Gly Gln Thr Val Ala Leu Val Gly Asn Ser Gly Cys Gly
            420                 425                 430

Lys Ser Thr Thr Val Gln Leu Met Gln Arg Leu Tyr Asp Pro Thr Glu
        435                 440                 445

Gly Met Val Ser Val Asp Gly Gln Asp Ile Arg Thr Ile Asn Val Arg
    450                 455                 460

Phe Leu Arg Glu Ile Ile Gly Val Val Ser Gln Glu Pro Val Leu Phe
465                 470                 475                 480

Ala Thr Thr Ile Ala Glu Asn Ile Arg Tyr Gly Arg Glu Asn Val Thr
                485                 490                 495

Met Asp Glu Ile Glu Lys Ala Val Lys Glu Ala Asn Ala Tyr Asp Phe
            500                 505                 510

Ile Met Lys Leu Pro His Lys Phe Asp Thr Leu Val Gly Glu Arg Gly
        515                 520                 525

Ala Gln Leu Ser Gly Gly Gln Lys Gln Arg Ile Ala Ile Ala Arg Ala
    530                 535                 540

Leu Val Arg Asn Pro Lys Ile Leu Leu Leu Asp Glu Ala Thr Ser Ala
545                 550                 555                 560

Leu Asp Thr Glu Ser Glu Ala Val Val Gln Val Ala Leu Asp Lys Ala
                565                 570                 575

Arg Lys Gly Arg Thr Thr Ile Val Ile Ala His Arg Leu Ser Thr Val
            580                 585                 590

Arg Asn Ala Asp Val Ile Ala Gly Phe Asp Asp Gly Val Ile Val Glu
        595                 600                 605

Lys Gly Asn His Asp Glu Leu Met Lys Glu Lys Gly Ile Tyr Phe Lys
    610                 615                 620

Leu Val Thr Met Gln Thr Ala Gly Asn Glu Val Glu Leu Glu Asn Ala
625                 630                 635                 640

Ala Asp Glu Ser Lys Ser Glu Ile Asp Ala Leu Glu Met Ser Ser Asn
                645                 650                 655

Asp Ser Arg Ser Ser Leu Ile Arg Lys Arg Ser Thr Arg Arg Ser Val
            660                 665                 670

Arg Gly Ser Gln Ala Gln Asp Arg Lys Leu Ser Thr Lys Glu Ala Leu
        675                 680                 685

Asp Glu Ser Ile Pro Pro Val Ser Phe Trp Arg Ile Met Lys Leu Asn
    690                 695                 700

Leu Thr Glu Trp Pro Tyr Phe Val Val Gly Val Phe Cys Ala Ile Ile
705                 710                 715                 720

Asn Gly Gly Leu Gln Pro Ala Phe Ala Ile Ile Phe Ser Lys Ile Ile
                725                 730                 735

Gly Val Phe Thr Arg Ile Asp Asp Pro Glu Thr Lys Arg Gln Asn Ser
            740                 745                 750

Asn Leu Phe Ser Leu Leu Phe Leu Ala Leu Gly Ile Ile Ser Phe Ile
        755                 760                 765

Thr Phe Phe Leu Gln Gly Phe Thr Phe Gly Lys Ala Gly Glu Ile Leu

```
                770             775             780
Thr Lys Arg Leu Arg Tyr Met Val Phe Arg Ser Met Leu Arg Gln Asp
785             790             795             800
Val Ser Trp Phe Asp Asp Pro Lys Asn Thr Thr Gly Ala Leu Thr Thr
                805             810             815
Arg Leu Ala Asn Asp Ala Ala Gln Val Lys Gly Ala Ile Gly Ser Arg
                820             825             830
Leu Ala Val Ile Thr Gln Asn Ile Ala Asn Leu Gly Thr Gly Ile Ile
                835             840             845
Ile Ser Phe Ile Tyr Gly Trp Gln Leu Thr Leu Leu Leu Leu Ala Ile
                850             855             860
Val Pro Ile Ile Ala Ile Ala Gly Val Val Glu Met Lys Met Leu Ser
865             870             875             880
Gly Gln Ala Leu Lys Asp Lys Lys Glu Leu Glu Gly Ser Gly Lys Ile
                885             890             895
Ala Thr Glu Ala Ile Glu Asn Phe Arg Thr Val Val Ser Leu Thr Gln
                900             905             910
Glu Gln Lys Phe Glu His Met Tyr Ala Gln Ser Leu Gln Val Pro Tyr
                915             920             925
Arg Asn Ser Leu Arg Lys Ala His Ile Phe Gly Ile Thr Phe Ser Phe
                930             935             940
Thr Gln Ala Met Met Tyr Phe Ser Tyr Ala Gly Cys Phe Arg Phe Gly
945             950             955             960
Ala Tyr Leu Val Ala His Lys Leu Met Ser Phe Glu Asp Val Leu Leu
                965             970             975
Val Phe Ser Ala Val Val Phe Gly Ala Met Ala Val Gly Gln Val Ser
                980             985             990
Ser Phe Ala Pro Asp Tyr Ala Lys Ala Lys Ile Ser Ala Ala His Ile
                995             1000            1005
Ile Met Ile Ile Glu Lys Thr Pro Leu Ile Asp Ser Tyr Ser Thr
1010            1015            1020
Glu Gly Leu Met Pro Asn Thr Leu Glu Gly Asn Val Thr Phe Gly
1025            1030            1035
Glu Val Val Phe Asn Tyr Pro Thr Arg Pro Asp Ile Pro Val Leu
1040            1045            1050
Gln Gly Leu Ser Leu Glu Val Lys Lys Gly Gln Thr Leu Ala Leu
1055            1060            1065
Val Gly Ser Ser Gly Cys Gly Lys Ser Thr Val Val Gln Leu Leu
1070            1075            1080
Glu Arg Phe Tyr Asp Pro Leu Ala Gly Lys Val Leu Leu Asp Gly
1085            1090            1095
Lys Glu Ile Lys Arg Leu Asn Val Gln Trp Leu Arg Ala His Leu
1100            1105            1110
Gly Ile Val Ser Gln Glu Pro Ile Leu Phe Asp Cys Ser Ile Ala
1115            1120            1125
Glu Asn Ile Ala Tyr Gly Asp Asn Ser Arg Val Val Ser Gln Glu
1130            1135            1140
Glu Ile Val Arg Ala Ala Lys Glu Ala Asn Ile His Ala Phe Ile
1145            1150            1155
Glu Ser Leu Pro Asn Lys Tyr Ser Thr Lys Val Gly Asp Lys Gly
1160            1165            1170
Thr Gln Leu Ser Gly Gly Gln Lys Gln Arg Ile Ala Ile Ala Arg
1175            1180            1185
```

```
Ala Leu Val Arg Gln Pro His Ile Leu Leu Asp Glu Ala Thr
    1190            1195                1200

Ser Ala Leu Asp Thr Glu Ser Glu Lys Val Val Gln Glu Ala Leu
    1205                1210                1215

Asp Lys Ala Arg Glu Gly Arg Thr Cys Ile Val Ile Ala His Arg
    1220                1225                1230

Leu Ser Thr Ile Gln Asn Ala Asp Leu Ile Val Val Phe Gln Asn
    1235                1240                1245

Gly Arg Val Lys Glu His Gly Thr His Gln Gln Leu Leu Ala Gln
    1250                1255                1260

Lys Gly Ile Tyr Phe Ser Met Val Ser Val Gln Ala Gly Thr Lys
    1265                1270                1275

Arg Gln
    1280

<210> SEQ ID NO 3
<211> LENGTH: 37
<212> TYPE: DNA
<213> ORGANISM: Homo sapiens

<400> SEQUENCE: 3
aagctggaga gatcctcacc aagcggctcc gatacat                       37

<210> SEQ ID NO 4
<211> LENGTH: 19
<212> TYPE: DNA
<213> ORGANISM: Homo sapiens

<400> SEQUENCE: 4
aagctggaga gatcctcac                                           19

<210> SEQ ID NO 5
<211> LENGTH: 17
<212> TYPE: DNA
<213> ORGANISM: Homo sapiens

<400> SEQUENCE: 5
aagcggctcc gatacat                                             17

<210> SEQ ID NO 6
<211> LENGTH: 38
<212> TYPE: DNA
<213> ORGANISM: Homo sapiens

<400> SEQUENCE: 6
aagctggaga gatcctcacc caagcggctc cgatacat                      38

<210> SEQ ID NO 7
<211> LENGTH: 14
<212> TYPE: DNA
<213> ORGANISM: Homo sapiens

<400> SEQUENCE: 7
cggctccgat acat                                                14

<210> SEQ ID NO 8
<211> LENGTH: 18
<212> TYPE: DNA
<213> ORGANISM: Homo sapiens

<400> SEQUENCE: 8
```

```
aagctggaga gatcctca                                              18

<210> SEQ ID NO 9
<211> LENGTH: 16
<212> TYPE: DNA
<213> ORGANISM: Homo sapiens

<400> SEQUENCE: 9
agcggctccg atacat                                                16

<210> SEQ ID NO 10
<211> LENGTH: 21
<212> TYPE: DNA
<213> ORGANISM: Homo sapiens

<400> SEQUENCE: 10
aagctggaga gatcctcacc a                                          21

<210> SEQ ID NO 11
<211> LENGTH: 15
<212> TYPE: DNA
<213> ORGANISM: Homo sapiens

<400> SEQUENCE: 11
gcggctccga tacat                                                 15

<210> SEQ ID NO 12
<211> LENGTH: 15
<212> TYPE: DNA
<213> ORGANISM: Homo sapiens

<400> SEQUENCE: 12
aagctggaga gatcc                                                 15

<210> SEQ ID NO 13
<211> LENGTH: 37
<212> TYPE: DNA
<213> ORGANISM: Homo sapiens

<400> SEQUENCE: 13
aagctggaga gatcctcacc aagcggctcc gatacat                         37

<210> SEQ ID NO 14
<211> LENGTH: 14
<212> TYPE: DNA
<213> ORGANISM: Homo sapiens

<400> SEQUENCE: 14
cggctccgat acat                                                  14

<210> SEQ ID NO 15
<211> LENGTH: 14
<212> TYPE: DNA
<213> ORGANISM: Homo sapiens

<400> SEQUENCE: 15
cggctccgat acat                                                  14

<210> SEQ ID NO 16
<211> LENGTH: 17
<212> TYPE: DNA
<213> ORGANISM: Homo sapiens
```

```
<400> SEQUENCE: 16
aagctggaga gatcctc                                                          17

<210> SEQ ID NO 17
<211> LENGTH: 15
<212> TYPE: DNA
<213> ORGANISM: Homo sapiens

<400> SEQUENCE: 17
aagctggaga gatcc                                                            15

<210> SEQ ID NO 18
<211> LENGTH: 17
<212> TYPE: DNA
<213> ORGANISM: Homo sapiens

<400> SEQUENCE: 18
aagcggctcc gatacat                                                          17

<210> SEQ ID NO 19
<211> LENGTH: 13
<212> TYPE: DNA
<213> ORGANISM: Homo sapiens

<400> SEQUENCE: 19
aagctggaga gat                                                              13

<210> SEQ ID NO 20
<211> LENGTH: 14
<212> TYPE: DNA
<213> ORGANISM: Homo sapiens

<400> SEQUENCE: 20
aagctggaga gatc                                                             14
```

TEPOXALIN TARGETING OF ABCB1 OVEREXPRESSING CANCERS

CROSS REFERENCE TO RELATED APPLICATIONS

This application is a national stage application, filed under 35 U.S.C. § 371, of international application No. PCT/US2019/060516, filed Nov. 8, 2019, which claims the benefit of U.S. Provisional Application No. 62/758,294, filed Nov. 9, 2018, entitled "Tepoxalin Targeting of ABCB1 Overexpressing Cancers," the entire contents of which are incorporated herein by reference.

SEQUENCE LISTING

The instant application contains a Sequence Listing which has been filed electronically in ASCII format and is hereby incorporated by reference in its entirety. Said ASCII copy, created on Nov. 25, 2024, is named BN00007_0742_SL.txt and is 19,929 Bytes in size.

FIELD OF THE INVENTION

The invention relates generally to methods, compositions and kits for the identification and treatment of ABCB1 overexpressing cancers.

BACKGROUND OF THE INVENTION

Identifying therapeutic compounds capable of killing neoplastic cells that have either developed or are at risk of developing resistance to primary therapies poses an ongoing challenge for the oncology field. A need exists for agents that are capable of blocking neoplastic cells from developing chemotherapeutic resistance and/or are capable of killing neoplastic cells that have developed resistance to primary therapies.

BRIEF SUMMARY OF THE INVENTION

The current disclosure relates, at least in part, to the identification of tepoxalin as a drug that exhibits enhanced killing of neoplasia cells that express high levels of the ABCB1 (MDR1) transporter. Elevated expression levels of the ABCB1 (MDR1) transporter have previously been associated with protecting neoplasia cell lines from chemotherapeutic drugs, and it has herein been identified that the chemotherapeutic drugs docetaxel, busulfan, carfilzomib, daunorubicin, doxorubicin, epirubicin, idarubicin, ixabepilone, paclitaxel, romidepsin, vincristine and vinorelbine all consistently exhibited more robust levels of cell killing when applied to neoplastic cells that expressed lower levels of ABCB1 and reduced (dampened) levels of cell killing when applied to neoplastic cells that expressed higher levels of ABCB1. This thus far unique property of tepoxalin, which is a drug that has been previously approved for treatment of osteoarthritis in dogs (tepoxalin also reached phase II human trials for osteoarthritis), has herein identified tepoxalin as a lead candidate compound for repurposing as a drug for prevention and/or treatment of cancer, either alone or in combination with other cancer therapies (optionally in combination with and/or following administration of chemotherapeutic drugs for which elevated ABCB1 expression tends to promote resistance of such cells to killing by such chemotherapeutic drugs). Treatable cancers include lung, large intestine, bone, ovarian, kidney, hepatic, biliary tract and thyroid cancers, among others. Compositions and methods for the diagnosis and treatment of subjects and/or cancers that are likely to be responsive to treatment with tepoxalin are therefore provided.

In one aspect, the instant disclosure provides a method for selecting a treatment for a subject having or at risk of developing a cancer, the method including (a) obtaining a sample from a subject having or at risk of developing a cancer; (b) identifying the presence or absence in the sample of high ABCB1 mRNA expression levels, high ABCB1 protein expression levels and/or amplification of the ABCB1 locus; and (c) selecting tepoxalin, a tepoxalin derivative, the tepoxalin metabolite RWJ20142 or a RWJ20142 derivative, as a treatment for the subject if high ABCB1 mRNA expression levels, high ABCB1 protein expression levels and/or amplification of the ABCB1 locus is observed in the sample, thereby selecting a treatment for the subject having or at risk of developing a cancer.

In one embodiment, the cancer is a lung, colorectal, kidney, hepatic, lymphoma, bone, ovarian, biliary tract or thyroid cancer.

In another embodiment, step (b) includes identifying the presence or absence in the sample of elevated ABCB1 mRNA expression, as compared to an appropriate control.

Optionally, tepoxalin is selected as a treatment for the subject.

In certain embodiments, the method further includes step (d): administering the selected tepoxalin, tepoxalin derivative, RWJ20142 or RWJ20142 derivative to the subject.

In one embodiment, step (c) further includes selecting a non-tepoxalin chemotherapeutic drug as a treatment for the subject. Optionally, the non-tepoxalin chemotherapeutic drug is docetaxel, busulfan, carfilzomib, daunorubicin, doxorubicin, epirubicin, idarubicin, ixabepilone, paclitaxel, romidepsin, vincristine or vinorelbine, or is a combination thereof.

In certain embodiments, identifying step (b) involves use of a kit as described herein.

In one embodiment, the subject is human.

Another aspect of the disclosure provides a method for selecting a treatment for a subject having or at risk of developing a cancer, the method involving selecting tepoxalin, a tepoxalin derivative, RWJ20142 or a RWJ20142 derivative as a treatment for the subject, thereby selecting a treatment for the subject having or at risk of developing a cancer.

In one embodiment, the method further includes administering tepoxalin, a tepoxalin derivative, RWJ20142 or a RWJ20142 derivative to the subject. Optionally, the method further includes administering a non-tepoxalin chemotherapeutic drug to the subject.

An additional aspect of the disclosure provides a method for treating or preventing cancer in a subject, the method involving (a) obtaining a sample from a subject having or at risk of developing cancer; (b) identifying the presence or absence in the sample of high ABCB1 mRNA expression levels, high ABCB1 protein expression levels and/or amplification of the ABCB1 locus; and (c) administering tepoxalin, a tepoxalin derivative, RWJ20142 or a RWJ20142 derivative to the subject if high ABCB1 mRNA expression levels, high ABCB1 protein expression levels and/or amplification of the ABCB1 locus is identified in the sample, thereby treating or preventing cancer in the subject.

A further aspect of the disclosure provides a method for treating a subject having a cancer that is resistant to a non-tepoxalin chemotherapeutic drug, the method involving administering to the subject tepoxalin, a tepoxalin derivative, RWJ20142 or a RWJ20142 derivative, thereby treating the subject having a cancer that is resistant to a non-tepoxalin chemotherapeutic drug.

Another aspect of the disclosure provides a method for treating or preventing cancer in a subject, the method involving co-administering to a subject having or at risk of developing cancer (i) tepoxalin, a tepoxalin derivative, RWJ20142 or a RWJ20142 derivative and (ii) a non-tepoxalin chemotherapeutic drug, thereby treating or preventing cancer in the subject.

An additional aspect of the disclosure provides a kit for identifying high expression of ABCB1 mRNA or protein in a sample, where the kit includes an oligonucleotide for detection of ABCB1 mRNA or an anti-ABCB1 antibody (optionally, the anti-ABCB1 antibody is labeled or the kit includes a labeled secondary antibody that binds the anti-ABCB1 antibody), as well as instructions for its use.

In certain embodiments, the sample is a cancer sample, or is a tissue sample of a subject having cancer.

Another aspect of the disclosure provides a pharmaceutical composition for treating a subject having cancer that includes a therapeutically effective amount of tepoxalin, a tepoxalin derivative, RWJ20142 or a RWJ20142 derivative and a pharmaceutically acceptable carrier.

In certain embodiments, the cancer is resistant to a non-tepoxalin chemotherapeutic drug.

Definitions

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value.

In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Unless otherwise clear from context, all numerical values provided herein are modified by the term "about."

The term "administration" refers to introducing a substance into a subject. In general, any route of administration may be utilized including, for example, parenteral (e.g., intravenous), oral, topical, subcutaneous, peritoneal, intraarterial, inhalation, vaginal, rectal, nasal, introduction into the cerebrospinal fluid, or instillation into body compartments. In some embodiments, administration is oral. Additionally or alternatively, in some embodiments, administration is parenteral. In some embodiments, administration is intravenous.

By "agent" is meant any small compound (e.g., small molecule), antibody, nucleic acid molecule, or polypeptide, or fragments thereof or cellular therapeutics such as allogeneic transplantation and/or CART-cell therapy.

The term "cancer" refers to a malignant neoplasm (Stedman's Medical Dictionary, 25th ed.; Hensyl ed.; Williams & Wilkins: Philadelphia, 1990). Exemplary cancers include, but are not limited to, melanoma and ovarian cancer (e.g., cystadenocarcinoma, ovarian embryonal carcinoma, ovarian adenocarcinoma), with ovarian cancer specifically including clear cell ovarian cancer. Additional exemplary cancers include, but are not limited to, colorectal cancer (e.g., colon cancer, rectal cancer, colorectal adenocarcinoma), endometrial cancer (e.g., uterine cancer, uterine sarcoma), esophageal cancer (e.g., adenocarcinoma of the esophagus, Barrett's adenocarcinoma), and gastric cancer (e.g., stomach adenocarcinoma (STAD)), including, e.g., colon adenocarcinoma (COAD), oesophageal carcinoma (ESCA), rectal adenocarcinoma (READ) and uterine corpus endometrial carcinoma (UCEC). Other exemplary forms of cancer include, but are not limited to, diffuse large B-cell lymphoma (DLBCL), as well as the broader class of lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma (DLBCL)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell lymphoma (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; hematopoietic cancers (e.g., myeloid malignancies (e.g., acute myeloid leukemia (AML) (e.g., B-cell AML, T-cell AML), myelodysplastic syndrome, myeloproliferative neoplasm, chronic myelomonocytic leukemia (CMML) and chronic myelogenous leukemia (CML) (e.g., B-cell CML, T-cell CML)) and lymphocytic leukemia such as acute lymphocytic leukemia (ALL) (e.g., B-cell ALL, T-cell ALL) and chronic lymphocytic leukemia (CLL) (e.g., B-cell CLL, T-cell CLL)); brain cancer (e.g., meningioma, glioblastomas, glioma (e.g., astrocytoma, oligodendroglioma), medulloblastoma); lung cancer (e.g., bronchogenic carcinoma, small cell lung cancer (SCLC), non-small cell lung cancer (NSCLC), adenocarcinoma of the lung); acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); bronchus cancer; carcinoid tumor; cervical cancer (e.g., cervical adenocarcinoma); choriocarcinoma; chordoma; craniopharyngioma; connective tissue cancer; epithelial carcinoma; ependymoma; endotheliosarcoma (e.g., Kaposi's sarcoma, multiple idiopathic hemorrhagic sarcoma); Ewing's sarcoma; ocular cancer (e.g., intraocular melanoma, retinoblastoma); familiar hypereosinophilia; gall bladder cancer; gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendocrine tumor (GEP-NET), carcinoid tumor); osteosarcoma (e.g., bone cancer); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

By "control" or "reference" is meant a standard of comparison. In one aspect, as used herein, "changed as compared to a control" sample or subject is understood as having a level that is statistically different than a sample from a normal, untreated, or control sample. Control samples include, for example, cells in culture, one or more laboratory test animals, or one or more human subjects. Methods to select and test control samples are within the ability of those in the art. Determination of statistical significance is within the ability of those skilled in the art, e.g., the number of standard deviations from the mean that constitute a positive result.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation.

As used herein, the term "next-generation sequencing" or "NGS" can refer to sequencing technologies that have the capacity to sequence polynucleotides at speeds that were unprecedented using conventional sequencing methods (e.g., standard Sanger or Maxam-Gilbert sequencing methods). These unprecedented speeds are achieved by performing and reading out thousands to millions of sequencing reactions in parallel. NGS sequencing platforms include, but are not limited to, the following: Massively Parallel Signature Sequencing (Lynx Therapeutics); 454 pyro-sequencing (454 Life Sciences/Roche Diagnostics); solid-phase, reversible dye-terminator sequencing (Solexa/Illumina); SOLiD technology (Applied Biosystems); Ion semiconductor sequencing (ion Torrent); and DNA nanoball sequencing (Complete Genomics). Descriptions of certain NGS platforms can be found in the following: Shendure, er al., "Next-generation DNA sequencing," Nature, 2008, vol. 26, No. 10, 135-1 145; Mardis, "The impact of next-generation sequencing technology on genetics," Trends in Genetics, 2007, vol. 24, No. 3, pp. 133-141; Su, et al., "Next-generation sequencing and its applications in molecular diagnostics" Expert Rev Mol Diagn, 2011, 11 (3):333-43; and Zhang et al., "The impact of next-generation sequencing on genomics", J Genet Genomics, 201, 38(3): 95-109.

As used herein, the term "non-tepoxalin chemotherapeutic drug" refers to any drug that can be employed in cancer therapy that is not any one of the following: tepoxalin, a tepoxalin derivative, tepoxalin metabolite RWJ20142 or a RWJ20142 derivative.

As used herein, the term "subject" includes humans and mammals (e.g., mice, rats, pigs, cats, dogs, and horses). In many embodiments, subjects are mammals, particularly primates, especially humans. In some embodiments, subjects are livestock such as cattle, sheep, goats, cows, swine, and the like; poultry such as chickens, ducks, geese, turkeys, and the like; and domesticated animals particularly pets such as dogs and cats. In some embodiments (e.g., particularly in research contexts) subject mammals will be, for example, rodents (e.g., mice, rats, hamsters), rabbits, primates, or swine such as inbred pigs and the like.

As used herein, the terms "treatment," "treating," "treat" and the like, refer to obtaining a desired pharmacologic and/or physiologic effect. The effect can be prophylactic in terms of completely or partially preventing a disease or symptom thereof and/or can be therapeutic in terms of a partial or complete cure for a disease and/or adverse effect attributable to the disease. "Treatment," as used herein, covers any treatment of a disease or condition in a mammal, particularly in a human, and includes: (a) preventing the disease from occurring in a subject which can be predisposed to the disease but has not yet been diagnosed as having it; (b) inhibiting the disease, i.e., arresting its development; and (c) relieving the disease, i.e., causing regression of the disease.

Unless specifically stated or obvious from context, as used herein, the term "or" is understood to be inclusive. Unless specifically stated or obvious from context, as used herein, the terms "a", "an", and "the" are understood to be singular or plural.

The phrase "pharmaceutically acceptable carrier" is art recognized and includes a pharmaceutically acceptable material, composition or vehicle, suitable for administering compounds of the present disclosure to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it is understood that the particular value forms another aspect. It is further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. It is also understood that throughout the application, data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

The term "pharmaceutically acceptable salts, esters, amides, and prodrugs" as used herein refers to those carboxylate salts, amino acid addition salts, esters, amides, and prodrugs of the compounds of the present disclosure which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the disclosure.

The term "salts" refers to the relatively non-toxic, inorganic and organic acid addition salts of compounds of the present disclosure. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate and laurylsulphonate salts, and the like. These may include cations based on the alkali and alkaline earth metals, such as sodium, lithium, potassium, calcium, magnesium, and the like, as well as non-toxic ammonium, tetramethylammonium, tetramethylammonium, methylamine, dimethylamine, trimethylamine, triethylamine, ethylamine, and the like. (See, for example, S. M. Barge et al., "Pharmaceutical Salts," J. Pharm. Sci., 1977, 66:1-19 which is incorporated herein by reference).

A "therapeutically effective amount" of an agent described herein is an amount sufficient to provide a therapeutic benefit in the treatment of a condition or to delay or minimize one or more symptoms associated with the condition. A therapeutically effective amount of an agent means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Other features and advantages of the disclosure will be apparent from the following description of the preferred embodiments thereof, and from the claims. Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. All published foreign patents and patent applications cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

BRIEF DESCRIPTION OF THE DRAWINGS

The following detailed description, given by way of example, but not intended to limit the disclosure solely to the specific embodiments described, may best be understood in conjunction with the accompanying drawings, in which:

FIG. 1A shows that docetaxel killing of neoplastic cells was most robust in neoplastic cells that expressed relatively low levels of ABCB1 (<0 log RPKM, with ABCB1 expression levels assessed by RNAseq), with the efficacy of docetaxel killing of neoplastic cells declining in neoplastic cells that exhibited higher levels of ABCB1 (>0 log RPKM, with progressively more inhibited docetaxel-mediated cell killing observed as ABCB1 levels exceeded 2.5 log RPKM and an apparent plateau in docetaxel-mediated cell killing observed in the 5.0 log RPKM to 7.5 log RPKM range). Notably, chemotherapeutic drugs busulfan, carfilzomib, daunorubicin, doxorubicin, epirubicin, idarubicin, ixabepilone, paclitaxel, romidepsin, vincristine and vinorelbine were observed to exhibit similarly more robust levels of cell killing in neoplastic cells that expressed lower levels of ABCB1 and correspondingly dampened cell killing of neoplastic cells that expressed higher levels of ABCB1. FIG. 1B shows that conversely, tepoxalin exhibited progressively increasing levels of cell killing of neoplastic cell lines as expression levels of ABCB1 increased. Notably, while lower levels of tepoxalin-mediated cell killing were observed in cells that exhibited lower expression levels of ABCB1 (e.g., RNAseq detected ABCB1 expression levels below 0 log RPKM), progressively increasing levels of tepoxalin-mediated cell killing were observed in cells that exhibited progressively higher expression levels of ABCB1 (e.g., RNAseq detected ABCB1 expression levels of 2.5 log RPKM and above).

FIG. 3 lists specific examples of ABCB1-expressing (MDR1-expressing) cell lines that were identified herein as sensitive to tepoxalin, with paired measured levels of ABCB1 expression and tepoxalin IC50 values shown for each such neoplasia cell line listed (COLO668_LUNG, LS1034_LARGE_INTESTINE, CADOES1_BONE, HCC1588_LUNG, OVTOKO_OVARY, RCC10RGB_KIDNEY, HCT15_LARGE_INTESTINE, JHH7_LIVER, LS513_LARGE_INTESTINE, SNU1079_BILIARY_TRACT, BEN_LUNG, TT_THYROID, VMRCRCW_KIDNEY, SNUC4_LARGE_INTESTINE AND HT55_LARGE_INTESTINE).

FIG. 5A shows the sensitive arm of such studies, while FIG. 5B shows the resistive arm of such studies.

FIGS. 6A to 6C demonstrate that ABCB1 knockout partially rescued tepoxalin-mediated cell killing in LS1034 colon cancer cells. FIG. 6A shows ABCB1 gDNA indel formation and recites the following sequences: 5'-AAGCTGGAGAGATCCTCACCAAGCGGCTCCGA-TACAT-3' (SEQ ID NO: 3); 5'-AAGCTGGAGAGATCCT-CAC-3' (SEQ ID NO: 4) and 5'-AAGCGGCTCCGATA-CAT-3' (SEQ ID NO: 5); 5'-AAGCTGGAGAGATCCTCACCCAAGCGGCTCC-GATACAT-3' (SEQ ID NO: 6); 5'-AAG-3' and 5'-CGGCTCCGATACAT-3' (SEQ ID NO: 7); 5'-AAGCTG-GAGAGATCCTCA-3' (SEQ ID NO: 8) and 5'-AGCGGCTCCGATACAT-3' (SEQ ID NO: 9); 5'-AAGCTGGAGAGATCCTCACCA-3' (SEQ ID NO: 10) and 5'-GCGGCTCCGATACAT-3' (SEQ ID NO: 11); 5'-AAGCTGGAGAGATCC-3' (SEQ ID NO: 12) and 5'-GATACAT-3'; 5'-AAGCTGGAGAGATCCTCAC-CAAGCGGCTCCGATACAT-3' (SEQ ID NO: 13); 5'-AAGCTGGAG-3' and 5'-CGGCTCCGATACAT-3' (SEQ ID NO: 14); 5'-AAGCTGGAG-3' and 5'-CGGCTCCGATA-CAT-3' (SEQ ID NO: 15); 5'-AAGCTGGAGAGATCCTC-3' (SEQ ID NO: 16) and 5'-CGATACAT-3'; 5'-AAGCTG-GAGAGATCC-3' (SEQ ID NO: 17) and 5'-AAGCGGCTCCGATACAT-3' (SEQ ID NO: 18); and 5'-AAGCTGGAGAGAT-3' (SEQ ID NO: 19) and 5'-ACAT-3'. FIG. 6B shows ABCB1 protein knockout. FIG. 6C shows observed tepoxalin dose response curves, for the indicated treatments.

FIGS. 7A and 7B demonstrate drug-mediated cell killing results, for the indicated chemotherapeutic agents, tepoxalin and/or the MDR1 (ABCB1) inhibitor elacridar. FIG. 7A shows dose response curves. FIG. 7B lists observed IC50 values for the cell killing effect.

FIG. 8 shows an expanded cell line viability comparison, for the indicated chemotherapeutic agents, tepoxalin and/or the MDR1 (ABCB1) inhibitor elacridar, with observed IC50 values for the cell killing effect shown across cell lines REC1, LS1034 and SL1034 cells subjected to CRISPR screening (either with a control sgRNA (sg GFP) or an ABCB1 knockout construct (sg ABCB1-2).

FIG. 9A shows dose response curves obtained for Kuramochi cells absent further ABCB1 modification. FIG. 9B shows dose response curves obtained for Kuramochi cells that were modified to overexpress ABCB1 ("Kuramochi-ABCB1" cells), at a 144 hour timepoint.

FIG. 10A shows synergy mapped to D-R (LOEWE) LS1034-120H: paclitaxel vs. elacridar. FIG. 10B shows synergy mapped to D-R (LOEWE) LS1034-120H: tepoxalin vs. elacridar.

DETAILED DESCRIPTION OF THE INVENTION

Figure 1A:
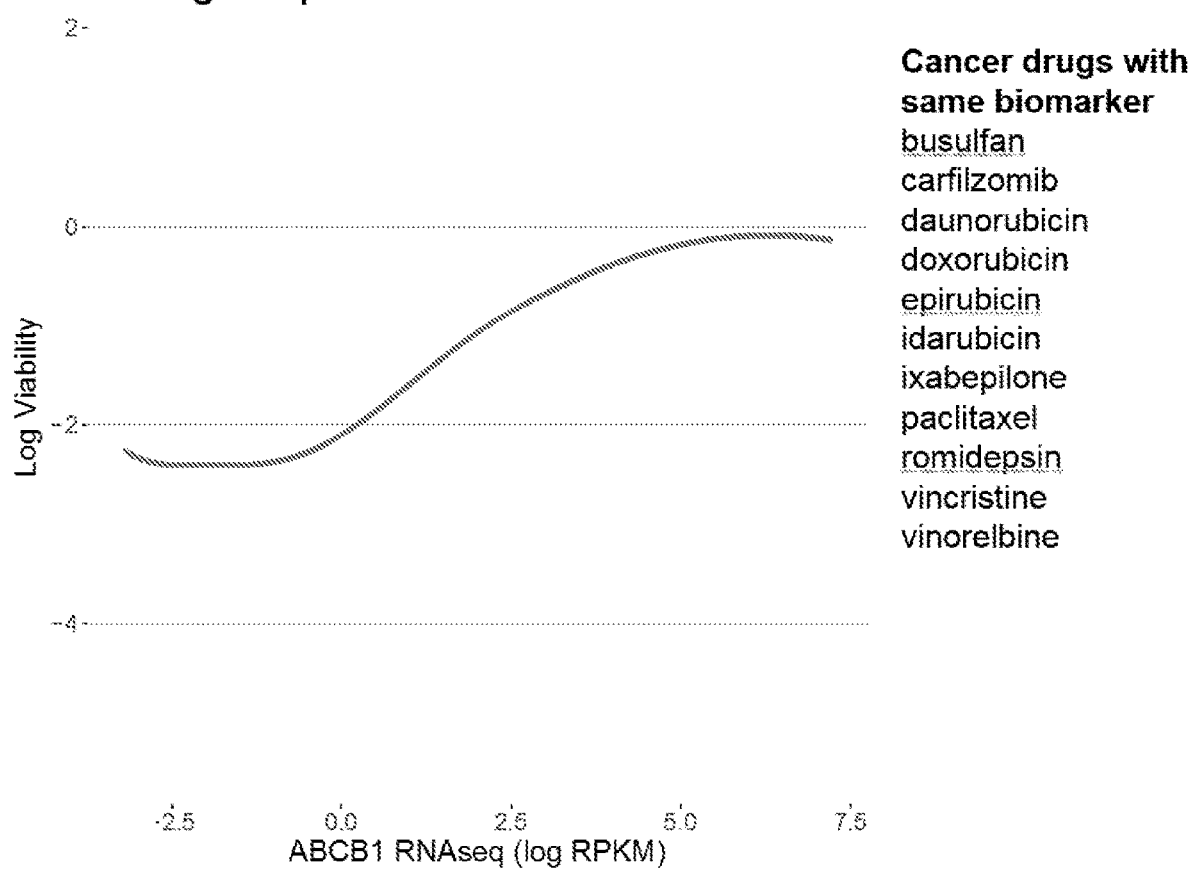
FIGS. 1A and 1B demonstrate that while high expression of ABCB1 (MDR1/p-glocoprotein) imparts a drug resistance phenotype to neoplastic cell lines treated with a number of art-recognized chemotherapeutic drugs, tepoxalin was identified as a drug with the unique property of inducing greater cell killing of neoplastic cell lines that exhibited increased levels of ABCB1 expression.

The present disclosure is directed, at least in part, to the discovery that certain types of cancer that have developed resistance to primary chemotherapeutic drugs—particularly where the chemotherapeutic drug-resistance has been imparted by amplification and/or overexpression of the MDR1 (ABCB1) pump—are particularly susceptible to tepoxalin. Indeed, tepoxalin was identified via genomic CRISPR screening methods as unique among drugs present in a drug repurposing library in exhibiting progressively enhanced killing of neoplasia cell lines as ABCB1 expression levels rose across such screened neoplasia cell lines. Cancers including lung, large intestine, bone, ovarian, kidney, hepatic, biliary tract and thyroid cancers, among others, have therefore herein been identified as susceptible to treatment with tepoxalin and/or tepoxalin metabolites (e.g., RWJ20142) or derivatives thereof, particularly those cancers that have developed resistance to primary chemotherapeutic drugs, especially those cancers for which MDR1 is amplified and/or MDR1 expression is elevated. The instant disclosure therefore provides compositions and methods for the diagnosis and treatment of cancer that employ tepoxalin and/or tepoxalin metabolites or derivatives thereof, either alone (i.e., as a monotherapy, optionally in certain classes of cancer) or in combination with other chemotherapeutic drugs (i.e., particularly in combination with non-tepoxalin chemotherapeutic drugs that are prone to having resistance develop in treated tumors, optionally wherein such chemotherapeutic resistance develops due to amplification and/or enhanced expression of ABCB1).

Many cancer types have intrinsic or acquired resistance to existing treatments (such as chemotherapy) due to high expression of drug efflux pumps. One pump known as ABCB1 (MDR1, p-glycoprotein) has the ability to transport many different chemotherapy and targeted therapy drugs, rendering tumors resistant. There is no current treatment specifically for cancers that express high levels of ABCB1 and this remains a critical area of unmet need in the clinic. The instant disclosure has identified a safe, existing drug (FDA-approved for use in animals; tested in human phase II clinical trials)—tepoxalin—that selectively kills cancer cell lines in a manner dependent on ABCB1 expression and activity. As also disclosed herein, ABCB1 expression can be used as a predictive biomarker to select patients for treatment.

The instant discovery was made using large-scale multiplex profiling of existing drugs against 578 cancer cell lines, employing a PRISM multiplexed cellular viability assay. Across more than 4,000 compounds, a single compound, tepoxalin, was identified for which high ABCB1 gene expression predicted cell line sensitivity. In confirmatory studies, it was identified that 1) ABCB1 was the most essential gene for tepoxalin killing in genome-wide CRISPR modifier screens, 2) ABCB1 over-expression sensitized resistant cells to tepoxalin and 3) other reference inhibitors of ABCB1 rescued cancer cells from tepoxalin. These results indicated that tepoxalin kills cancer cells in a manner dependent on ABCB1 activity, likely through a direct binding interaction.

Resistance to chemotherapy, often mediated by ABCB1, remains a critical unmet need in oncology. Disclosed herein is the concept of using tepoxalin to treat cancers with high mRNA expression, high protein expression and/or amplification of ABCB1. Tepoxalin- and/or tepoxalin derivative-targeted cancers include cancers that exhibit high ABCB1 expression at baseline or high expression following prior cancer treatment. Target cancer types include both solid tumors and hematopoietic cancers—such cancers include, but are not limited to, e.g., colorectal cancer, kidney cancer, liver cancer and lymphoma, among others.

Tepoxalin has previously been described as an agent for treatment of certain animal cancers in a non-specific manner, particularly in dog sarcoma models (PMID 24813477, PMID 22287649) and feline squamous cell carcinoma (PMID 21962280). The structure of tepoxalin is presented in FIG. 2.

The MDR1 (ABCB1) inhibitor elacridar has the following structure:

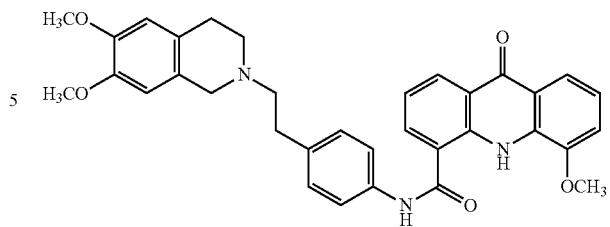

Identification of ABCB1 Overexpressing and/or ABCB1 Amplified Cells, Tissues and/or Cancers Identification of a tissue, tumor and/or cancer of a subject as exhibiting amplification of the ABCB1 locus and/or elevated levels of ABCB1 expression (including ABCB1 overexpression) can be performed by any method available in the art. Gene/genomic amplification events can be identified via genomic sequencing and/or genotyping approaches (including next-generation sequencing approaches), among others. Certain methods and compositions described herein relate to identification of a cell, cell line, sample, tissue and/or subject having or at risk of developing a cancer as exhibiting elevated levels of ABCB1 expression (including ABCB1 overexpression) at the mRNA or protein level, based upon gene-specific assessment of ABCB1 mRNA or protein performed upon the cell, cell line, sample, tissue and/or subject having or at risk of developing a cancer that exhibits elevated levels of ABCB1 expression. In certain embodiments, detection of elevated ABCB1 levels can readily be performed, e.g., via assessment of mRNA expression levels (e.g., via real-time PCR or other such quantitative method). In related embodiments, assessment of ABCB1 mRNA expression can be performed via art-recognized, oligonucleotide-mediated approaches, including, e.g., Northern blotting, expression profiling using RT-PCR and/or next-generation sequencing performed upon cellular transcriptomes.

In some embodiments, detection of elevated ABCB1 levels can readily be performed, e.g., via immunoassay for detection of ABCB1 protein levels.

Protein levels of ABCB1 can be quantitated in a variety of ways well known in the art, such as immunoprecipitation, Western blot analysis (immunoblotting), ELISA or fluorescence-activated cell sorting (FACS). Antibodies directed to ABCB1 can be identified and obtained from a variety of sources, such as the MSRS catalog of antibodies (Aerie Corporation, Birmingham, Mich.), or can be prepared via conventional antibody generation methods. Methods for preparation of polyclonal antisera are taught in, for example, Ausubel, F. M. et al., Current Protocols in Molecular Biology, Volume 2, pp. 11.12.1-11.12.9, John Wiley & Sons, Inc., 1997. Preparation of monoclonal antibodies is taught in, for example, Ausubel, F. M. et al., Current Protocols in Molecular Biology, Volume 2, pp. 11.4.1-11.11.5, John Wiley & Sons, Inc., 1997.

Immunoprecipitation methods are standard in the art and can be found at, for example, Ausubel, F. M. et al., Current Protocols in Molecular Biology, Volume 2, pp. 10.16.1-10.16.11, John Wiley & Sons, Inc., 1998. Western blot (immunoblot) analysis is standard in the art and can be found at, for example, Ausubel, F. M. et al., Current Protocols in Molecular Biology, Volume 2, pp. 10.8.1-10.8.21, John Wiley & Sons, Inc., 1997. Enzyme-linked immunosorbent assays (ELISA) are standard in the art and can be found at, Chemotherapeutic Drug-Resistant Cancers A number of cancers have been described in the art as capable of developing resistance to chemotherapeutic drugs (particularly chemotherapeutic drugs as monotherapy). As noted herein, exemplary types of cancer that have been identified to achieve chemotherapeutic drug resistance via elevated expression of MDR1 (ABCB1) include lung, colorectal, kidney, hepatic, lymphoma, bone, ovarian, biliary tract and thyroid cancers. The range of cancers presently contemplated as treatable using tepoxalin and/or tepoxalin-related compounds as described herein is not in any way limited to these aforementioned types of cancer.

As used in this context, to "treat" means to ameliorate at least one symptom of the cancer. For example, a treatment can result in a reduction in tumor size, tumor growth, cancer cell number, cancer cell growth, or metastasis or risk of metastasis.

For example, the methods can include selecting and/or administering a treatment that includes a therapeutically effective amount of tepoxalin and/or other agent capable of selectively killing cells that exhibit high mRNA expression, high protein expression and/or amplification of ABCB1. In certain embodiments, tepoxalin and/or other agent capable of selectively killing cells that exhibit high mRNA expression, high protein expression and/or amplification of ABCB1 may be administered in combination with an additional therapeutic agent, optionally a chemotherapeutic agent including docetaxel, busulfan, carfilzomib, daunorubicin, doxorubicin, epirubicin, idarubicin, ixabepilone, paclitaxel, romidepsin, vincristine or vinorelbine, and/or including platinum agents such as cisplatin or carboplatin, or other chemotherapeutic agents.

Exemplary human ABCB1 (MDR1) mRNA and protein sequences are:

*Homo sapiens* ATP binding cassette subfamily B member 1 (ABCB1), transcript variant 4, mRNA, Accession No. NM_001348946.1

(SEQ ID NO: 1):
GCTCATTCGAGTAGCGGCTCTTCCAAGCTCAAAGAAGCAGAGGCCGCTG

TTCGTTTCCTTTAGGTCTTTCCACTAAAGTCGGAGTATCTTCTTCCAAA

ATTTCACGTCTTGGTGGCCGTTCCAAGGAGCGCGAGGTCGGAATGGATC

TTGAAGGGGACCGCAATGGAGGAGCAAAGAAGAAGAACTTTTTTAAACT

GAACAATAAAAGTGAAAAAGATAAGAAGGAAAAGAAACCAACTGTCAGT

GTATTTTCAATGTTTCGCTATTCAAATTGGCTTGACAAGTTGTATATGG

TGGTGGGAACTTTGGCTGCCATCATCCATGGGGCTGGACTTCCTCTCAT

GATGCTGGTGTTTGGAGAAATGACAGATATCTTTGCAAATGCAGGAAAT

TTAGAAGATCTGATGTCAAACATCACTAATAGAAGTGATATCAATGATA

CAGGGTTCTTCATGAATCTGGAGGAAGACATGACCAGGTATGCCTATTA

TTACAGTGGAATTGGTGCTGGGGTGCTGGTTGCTGCTTACATTCAGGTT

TCATTTTGGTGCCTGGCAGCTGGAAGACAAATACACAAAATTAGAAAAC

AGTTTTTTCATGCTATAATGCGACAGGAGATAGGCTGGTTTGATGTGCA

CGATGTTGGGGAGCTTAACACCCGACTTACAGATGATGTCTCCAAGATT

AATGAAGGAATTGGTGACAAAATTGGAATGTTCTTTCAGTCAATGGCAA

CATTTTTCACTGGGTTTATAGTAGGATTTACACGTGGTTGGAAGCTAAC

CCTTGTGATTTTGGCCATCAGTCCTGTTCTTGGACTGTCAGCTGCTGTC

TGGGCAAAGATACTATCTTCATTTACTGATAAAGAACTCTTAGCGTATG

CAAAAGCTGGAGCAGTAGCTGAAGAGGTCTTGGCAGCAATTAGAACTGT

GATTGCATTTGGAGGACAAAAGAAAGAACTTGAAAGGTACAACAAAAAT

TTAGAAGAAGCTAAAAGAATTGGGATAAAGAAAGCTATTACAGCCAATA

TTTCTATAGGTGCTGCTTTCCTGCTGATCTATGCATCTTATGCTCTGGC

CTTCTGGTATGGGACCACCTTGGTCCTCTCAGGGGAATATTCTATTGGA

CAAGTACTCACTGTATTCTTTTCTGTATTAATTGGGGCTTTTAGTGTTG

GACAGGCATCTCCAAGCATTGAAGCATTTGCAAATGCAAGAGGAGCAGC

TTATGAAATCTTCAAGATAATTGATAATAAGCCAAGTATTGACAGCTAT

TCGAAGAGTGGGCACAAACCAGATAATATTAAGGGAAATTTGGAATTCA

GAAATGTTCACTTCAGTTACCCATCTCGAAAAGAAGTTAAGATCTTGAA

GGGTCTGAACCTGAAGGTGCAGAGTGGGCAGACGGTGGCCCTGGTTGGA

AACAGTGGCTGTGGGAAGAGCACAACAGTCCAGCTGATGCAGAGGCTCT

ATGACCCCACAGAGGGGATGGTCAGTGTTGATGGACAGGATATTAGGAC

CATAAATGTAAGGTTTCTACGGGAAATCATTGGTGTGGTGAGTCAGGAA

CCTGTATTGTTTGCCACCACGATAGCTGAAAACATTCGCTATGGCCGTG

AAAATGTCACCATGGATGAGATTGAGAAAGCTGTCAAGGAAGCCAATGC

CTATGACTTTATCATGAAACTGCCTCATAAATTTGACACCCTGGTTGGA

GAGAGAGGGCCCAGTTGAGTGGTGGGCAGAAGCAGAGGATCGCCATTG

CACGTGCCCTGGTTCGCAACCCCAAGATCCTCCTGCTGGATGAGGCCAC

GTCAGCCTTGGACACAGAAAGCGAAGCAGTGGTTCAGGTGGCTCTGGAT

AAGGCCAGAAAAGGTCGGACCACCATTGTGATAGCTCATCGTTTGTCTA

CAGTTCGTAATGCTGACGTCATCGCTGGTTTCGATGATGGAGTCATTGT

GGAGAAAGGAAATCATGATGAACTCATGAAAGAGAAAGGCATTTACTTC

AAACTTGTCACAATGCAGACAGCAGGAAATGAAGTTGAATTAGAAAATG

CAGCTGATGAATCCAAAAGTGAAATTGATGCCTTGGAAATGTCTTCAAA

TGATTCAAGATCCAGTCTAATAAGAAAAAGATCAACTCGTAGGAGTGTC

CGTGGATCACAAGCCCAAGACAGAAAGCTTAGTACCAAAGAGGCTCTGG

ATGAAAGTATACCTCCAGTTTCCTTTTGGAGGATTATGAAGCTAAATTT

AACTGAATGGCCTTATTTTGTTGTTGGTGTATTTTGTGCCATTATAAAT

GGAGGCCTGCAACCAGCATTTGCAATAATATTTTCAAAGATTATAGGGG

TTTTTACAAGAATTGATGATCCTGAAACAAAACGACAGAATAGTAACTT

GTTTTCACTATTGTTTCTAGCCCTTGGAATTATTTCTTTTATTACATTT

TTCCTTCAGGGTTTCACATTTGGCAAAGCTGGAGAGATCCTCACCAAGC

GGCTCCGATACATGGTTTTCCGATCCATGCTCAGACAGGATGTGAGTTG

GTTTGATGACCCTAAAAACACCACTGGAGCATTGACTACCAGGCTCGCC

AATGATGCTGCTCAAGTTAAAGGGCTATAGGTTCCAGGCTTGCTGTAA

TTACCCAGAATATAGCAAATCTTGGGACAGGAATAATTATATCCTTCAT

-continued
```
CTATGGTTGGCAACTAACACTGTTACTCTTAGCAATTGTACCCATCATT

GCAATAGCAGGAGTTGTTGAAATGAAAATGTTGTCTGGACAAGCACTGA

AAGATAAGAAAGAACTAGAAGGTTCTGGGAAGATCGCTACTGAAGCAAT

AGAAAACTTCCGAACCGTTGTTTCTTTGACTCAGGAGCAGAAGTTTGAA

CATATGTATGCTCAGAGTTTGCAGGTACCATACAGAAACTCTTTGAGGA

AAGCACACATCTTTGGAATTACATTTTCCTTCACCCAGGCAATGATGTA

TTTTTCCTATGCTGGATGTTTCCGGTTTGGAGCCTACTTGGTGGCACAT

AAACTCATGAGCTTTGAGGATGTTCTGTTAGTATTTTCAGCTGTTGTCT

TTGGTGCCATGGCCGTGGGGCAAGTCAGTTCATTTGCTCCTGACTATGC

CAAAGCCAAAATATCAGCAGCCCACATCATCATGATCATTGAAAAAACC

CCTTTGATTGACAGCTACAGCACGGAAGGCCTAATGCCGAACACATTGG

AAGGAAATGTCACATTTGGTGAAGTTGTATTCAACTATCCCACCCGACC

GGACATCCCAGTGCTTCAGGGACTGAGCCTGGAGGTGAAGAAGGGCCAG

ACGCTGGCTCTGGTGGGCAGCAGTGGCTGTGGGAAGAGCACAGTGGTCC

AGCTCCTGGAGCGGTTCTACGACCCCTTGGCAGGGAAAGTGCTGCTTGA

TGGCAAAGAAATAAAGCGACTGAATGTTCAGTGGCTCCGAGCACACCTG

GGCATCGTGTCCCAGGAGCCCATCCTGTTTGACTGCAGCATTGCTGAGA

ACATTGCCTATGGAGACAACAGCCGGGTGGTGTCACAGGAAGAGATTGT

GAGGGCAGCAAAGGAGGCCAACATACATGCCTTCATCGAGTCACTGCCT

AATAAATATAGCACTAAAGTAGGAGACAAAGGAACTCAGCTCTCTGGTG

GCCAGAAACAACGCATTGCCATAGCTCGTGCCCTTGTTAGACAGCCTCA

TATTTTGCTTTTGGATGAAGCCACGTCAGCTCTGGATACAGAAAGTGAA

AAGGTTGTCCAAGAAGCCCTGGACAAAGCCAGAGAAGGCCGACACCTGCA

TTGTGATTGCTCACCGCCTGTCCACCATCCAGAATGCAGACTTAATAGT

GGTGTTTCAGAATGGCAGAGTCAAGGAGCATGGCACGCATCAGCAGCTG

CTGGCACAGAAAGGCATCTATTTTTCAATGGTCAGTGTCCAGGCTGGAA

CAAAGCGCCAGTGAACTCTGACTGTATGAGATGTTAAATACTTTTTAAT

ATTTGTTTAGATATGACATTTATTCAAAGTTAAAAGCAAACACTTACAG

AATTATGAAGAGGTATCTGTTTAACATTTCCTCAGTCAAGTTCAGAGTC

TTCAGAGACTTCGTAATTAAAGGAACAGAGTGAGAGACATCATCAAGTG

GAGAGAAATCATAGTTTAAACTGCATTATAAATTTTATAACAGAATTAA

AGTAGATTTTAAAAGATAAAATGTGTAATTTTGTTTATATTTTCCCATT

TGGACTGTAACTGACTGCCTTGCTAAAAGATTATAGAAGTAGCAAAAAG

TATTGAAATGTTTGCATAAAGTGTCTATAATAAAACTAAACTTTCATGT

GA
```

*Homo sapiens* ATP binding cassette subfamily B member 1 (ABCB1) protein, Accession No. NP_001335875.1

```
(SEQ ID NO: 2):
MDLEGDRNGGAKKKNFFKLNNKSEKDKKEKKPTVSVFSMFRYSNWLDKL

YMVVGTLAAIIHGAGLPLMMLVFGEMTDIFANAGNLEDLMSNITNRSDI

NDTGFFMNLEEDMTRYAYYYSGIGAGVLVAAYIQVSFWCLAAGRQIHKI

RKQFFHAIMRQEIGWFDVHDVGELNTRLTDDVSKINEGIGDKIGMFFQS

MATFFTGFIVGFTRGWKLTLVILAISPVLGLSAAVWAKILSSFTDKELL

AYAKAGAVAEEVLAAIRTVIAFGGQKKELERYNKNLEEAKRIGIKKAIT

ANISIGAAFLLIYASYALAFWYGTTLVLSGEYSIGQVLTVFFSVLIGAF

SVGQASPSIEAFANARGAAYEIFKIIDNKPSIDSYSKSGHKPDNIKGNL

EFRNVHFSYPSRKEVKILKGLNLKVQSGQTVALVGNSGCGKSTTVQLMQ

RLYDPTEGMVSVDGQDIRTINVRFLREIIGVVSQEPVLFATTIAENIRY

GRENVTMDEIEKAVKEANAYDFIMKLPHKFDTLVGERGAQLSGGQKQRI

AIARALVRNPKILLLDEATSALDTESEAVVQVALDKARKGRTTIVIAHR

LSTVRNADVIAGFDDGVIVEKGNHDELMKEKGIYFKLVTMQTAGNEVEL

ENAADESKSEIDALEMSSNDSRSSLIRKRSTRRSVRGSQAQDRKLSTKE

ALDESIPPVSFWRIMKLNLTEWPYFVVGVFCAIINGGLQPAFAIIFSKI

IGVFTRIDDPETKRQNSNLFSLLFLALGIISFITFFLQGFTFGKAGEIL

TKRLRYMVFRSMLRQDVSWFDDPKNTTGALTTRLANDAAQVKGAIGSRL

AVITQNIANLGTGIIISFIYGWQLTLLLLAIVPIIAIAGVVEMKMLSGQ

ALKDKKELEGSGKIATEAIENFRTVVSLTQEQKFEHMYAQSLQVPYRNS

LRKAHIFGITFSFTQAMMYFSYAGCFRFGAYLVAHKLMSFEDVLLVFSA

VVFGAMAVGQVSSFAPDYAKAKISAAHIIMIIEKTPLIDSYSTEGLMPN

TLEGNVTFGEVVFNYPTRPDIPVLQGLSLEVKKGQTLALVGSSGCGKST

VVQLLERFYDPLAGKVLLDGKEIKRLNVQWLRAHLGIVSQEPILFDCSI

AENIAYGDNSRVVSQEEIVRAAKEANIHAFIESLPNKYSTKVGDKGTQL

SGGQKQRIAIARALVRQPHILLLDEATSALDTESEKVVQEALDKAREGR

TCIVIAHRLSTIQNADLIVVFQNGRVKEHGTHQQLLAQKGIYFSMVSVQ

AGTKRQ
```

An "effective amount" is an amount sufficient to effect beneficial or desired results. For example, a therapeutic amount is one that achieves the desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a therapeutic compound (i.e., an effective dosage) depends on the therapeutic compounds selected. The compositions can be administered from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments.

Dosage, toxicity and therapeutic efficacy of the therapeutic compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of tepoxalin, or a metabolite or derivative thereof, which achieves a half-maximal inhibition of symptoms and/or a half-maximal extent of killing of targeted cancer cells) as determined in cell culture. Such information can be used to more accurately determine useful doses in humans. Levels in plasma may be measured, for example, by high performance liquid chromatography.

Combination Treatments

The compositions and methods of the present disclosure may be used in the context of a number of therapeutic or prophylactic applications. In order to increase the effectiveness of a treatment with the compositions of the present disclosure, e.g., tepoxalin, a tepoxalin derivative, RWJ20142 or a RWJ20142 derivative selected and/or administered as a single agent, or to augment the efficacy of another therapy (second therapy), it may be desirable to combine these compositions and methods with one another, or with other agents and methods effective in the treatment, amelioration, or prevention of diseases and pathologic conditions, for example, cancers that are prone to developing ABCB1-mediated resistance.

In certain embodiments of the instant disclosure, one or more chemotherapeutic drugs that are unrelated to tepoxalin can be co-administered with tepoxalin, or can be administered in advance of tepoxalin administration. Examples of such non-tepoxalin chemotherapeutics include docetaxel, busulfan, carfilzomib, daunorubicin, doxorubicin, epirubicin, idarubicin, ixabepilone, paclitaxel, romidepsin, vincristine and vinorelbine, each of which has been disclosed herein as being susceptible to ABCB1 overexpression-mediated rescue of chemotherapeutic drug-targeted cancer cells.

Docetaxel has the following structure:

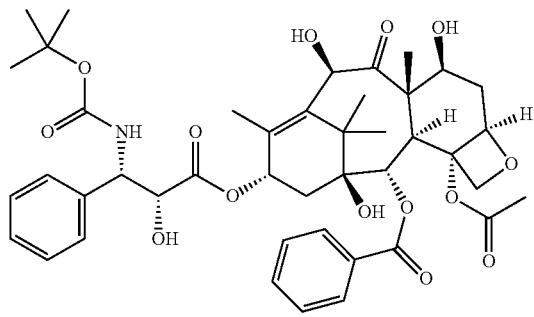

Exemplary FDA-approved dose regimens for docetaxel include the following:

Breast Cancer
    60 mg/m² to 100 mg/m² single agent
    75 mg/m² administered 1 hour after doxorubicin 50 mg/m² and cyclophosphamide 500 mg/m² every 3 weeks for 6 cycles Non-Small Cell Lung Cancer
    after platinum therapy failure: 75 mg/m² single agent
    chemotherapy-naive: 75 mg/m² followed by cisplatin 75 mg/m²

Prostate cancer
    75 mg/m² with 5 mg prednisone twice a day continuously

Gastric Adenocarcinoma
    75 mg/m² followed by cisplatin 75 mg/m² (both on day 1 only) followed by fluorouracil 750 mg/m² per day as a 24-hr intravenous infusion (days 1-5), starting at end of cisplatin infusion Head and Neck Cancer
    75 mg/m² followed by cisplatin 75 mg/m² intravenously (day 1), followed by fluorouracil 750 mg/m² per day as a 24-hr intravenous infusion (days 1-5), starting at end of cisplatin infusion; for 4 cycles
    75 mg/m² followed by cisplatin 100 mg/m² intravenously (day 1), followed by fluorouracil 1000 mg/m² per day as a 24-hr intravenous infusion (days 1-4); for 3 cycles Docetaxel is also being investigated to treat small cell lung, ovarian, bladder, and pancreatic cancers, soft tissue sarcoma and melanoma.

Busulfan has the following structure:

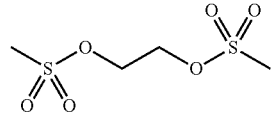

Exemplary dose regimens for docetaxel include the following:

For chronic myelogenous leukemia (CML), the recommended adult dose is 0.8 mg per kg of ideal body weight or actual body weight, whichever is lower, administered intravenously via a central venous catheter as a two-hour infusion every six hours for four consecutive days for a total of 16 doses.

Carfilzomib has the following structure:

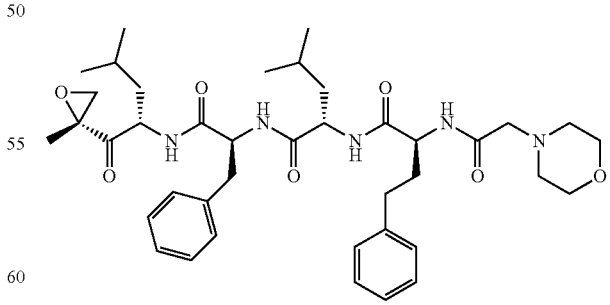

Exemplary FDA-approved carfilzomib dose regimens include:

For multiple myeloma, carfilzomib is administered intravenously over 2 to 10 minutes, on two consecutive days, each week for three weeks (Days 1, 2, 8, 9, 15, and 16), followed by a 12-day rest period (Days 17 to 28). Each 28-day period is considered one treatment cycle.

In Cycle 1, carfilzomib is administered at a dose of 20 mg/m². If tolerated in Cycle 1, the dose should be escalated to 27 mg/m² beginning in Cycle 2 and continued at 27 mg/m² in subsequent cycles. Treatment may be continued until disease progression or until unacceptable toxicity occurs.

The dose is calculated using the patient's actual body surface area at baseline. Patients with a body surface area greater than 2.2 m² should receive a dose based upon a body surface area of 2.2 m².

Daunorubicin has the following structure:

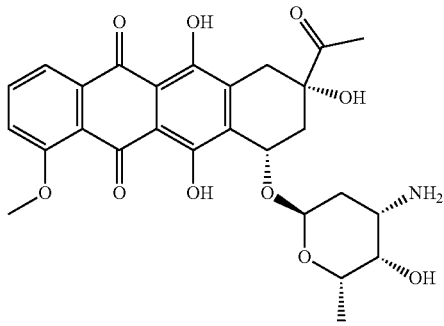 [SMILES: COc1cccc2c1C(=O)c1c(O)c3c(c(O)c1C2=O)C[C@@](O)(C(C)=O)C[C@@H]3O[C@H]1C[C@H](N)[C@H](O)[C@H](C)O1]

Exemplary FDA-approved daunorubicin dose regimens include the following, for acute myeloid leukemia (t-AML) or AML with myelodysplasia-related changes (AML-MRC)

Induction: VYXEOS (daunorubicin 44 mg/m² and cytarabine 100 mg/m²) liposome via intravenous infusion over 90 minutes on days 1, 3, and 5 and on days 1 and 3 for subsequent cycles of induction, if needed.

Consolidation: VYXEOS (daunorubicin 29 mg/m² and cytarabine 65 mg/m²) liposome via intravenous infusion over 90 minutes on days 1 and 3.

Doxorubicin has the following structure:

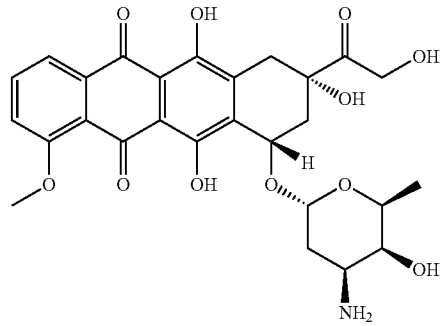 [SMILES: COc1cccc2c1C(=O)c1c(O)c3c(c(O)c1C2=O)C[C@@](O)(C(=O)CO)C[C@@H]3O[C@H]1C[C@H](N)[C@H](O)[C@H](C)O1]

Exemplary FDA-approved doxorubicin dose regimens include the following, for e.g., breast cancer, bladder cancer, Kaposi's sarcoma, lymphoma, and acute lymphocytic leukemia:

The most commonly used dose schedule when used as a single agent is 60 to 75 mg/m² as a single intravenous injection administered at 21-day intervals. The lower dosage should be given to patients with inadequate marrow reserves due to old age, or prior therapy, or neoplastic marrow infiltration.

When used in combination with other chemotherapy drugs, the most commonly used dosage of doxorubicin is 40 to 60 mg/m² given as a single intravenous injection every 21 to 28 days.

Epirubicin has the following structure:

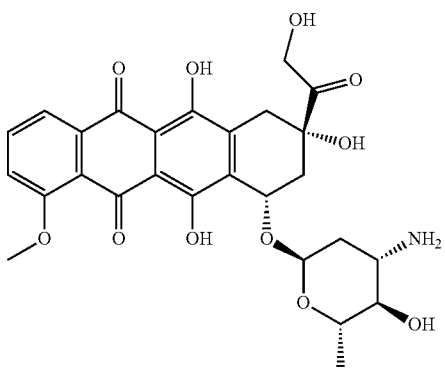 [SMILES: COc1cccc2c1C(=O)c1c(O)c3c(c(O)c1C2=O)C[C@@](O)(C(=O)CO)C[C@@H]3O[C@H]1C[C@H](N)[C@@H](O)[C@H](C)O1]

Exemplary epirubicin dose regimens include the following, for breast cancer:

Administer intravenously in repeated 3- to 4-week cycles, either total dose on Day 1 of each cycle or divided equally and given on Days 1 and 8 of each cycle.

The recommended starting dose is 100 to 120 mg/m². Dosage reductions are possible when given in certain combinations.

Idarubicin has the following structure:

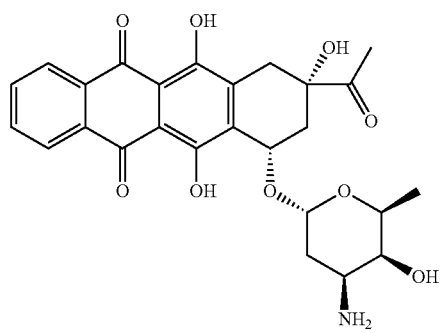 [SMILES: CC(=O)[C@]1(O)Cc2c(O)c3c(c(O)c2[C@@H](O[C@H]2C[C@H](N)[C@H](O)[C@H](C)O2)C1)C(=O)c1ccccc1C3=O]

Exemplary idarubicin dose regimens include the following, for acute myeloid leukemia:

12 mg/m² daily for 3 days by slow (10 to 15 min) intravenous injection in combination with cytarabine. The cytarabine may be given as 100 mg/m² daily by continuous infusion for 7 days or as cytarabine 25 mg/m² intravenous bolus followed by cytarabine 200 mg/m² daily for 5 days continuous infusion.

Ixabepilone has the following structure:

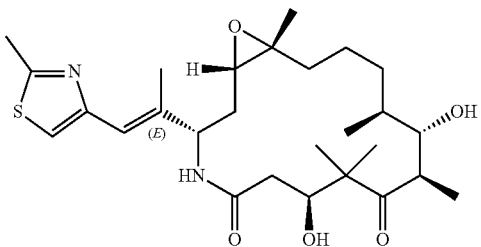

Exemplary ixabepilone dose regimens include the following, for treatment of metastatic or locally advanced breast cancer:

The recommended dose is 40 mg/m² infused intravenously over 3 hours every 3 weeks.

Paclitaxel has the following structure:

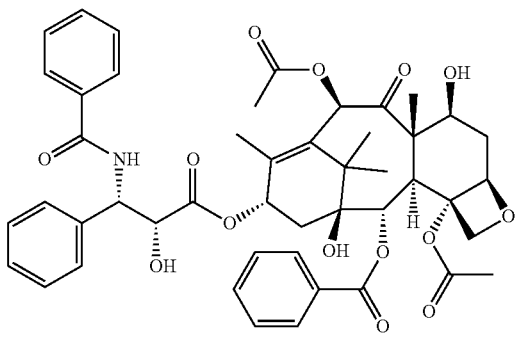 [SMILES: CC(=O)O[C@H]1C(=O)[C@@]2(C)[C@H]([C@H](OC(=O)c3ccccc3)[C@]3(O)C[C@H](OC(=O)[C@H](O)[C@@H](NC(=O)c4ccccc4)c4ccccc4)C(C)=C1C3(C)C)[C@]1(OC(C)=O)CO[C@@H]1C[C@@H]2O]

Exemplary paclitaxel dose regimens include the following, for treatment of ovarian cancer, breast cancer, lung cancer, Kaposi sarcoma, cervical cancer, and pancreatic cancer:

Administered intravenously over 3 hours at a dose of 175 mg/m² followed by cisplatin at a dose of 75 mg/m² or intravenously over 24 hours at a dose of 135 mg/m² followed by cisplatin at a dose of 75 mg/m².

Romidepsin has the following structure:

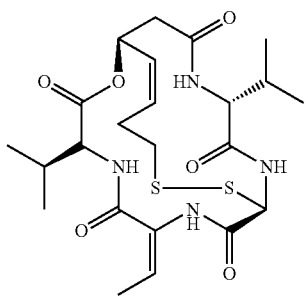

Exemplary romidepsin dose regimens include the following, for treatment of cutaneous T-cell lymphoma (CTCL):

14 mg/m² administered intravenously (IV) over a 4-hour period on days 1, 8 and 15 of a 28-day cycle.

Vincristine has the following structure:

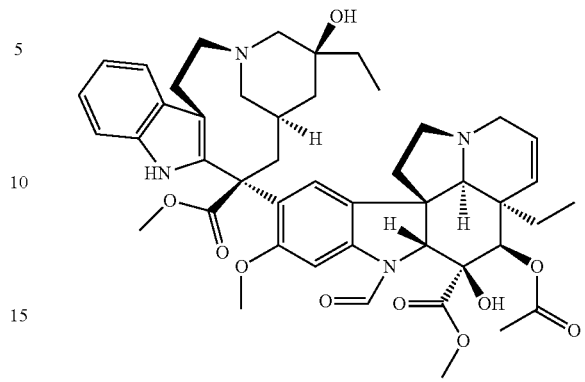

Exemplary dose regimens for vincristine include the following, for treatment of Philadelphia chromosome-negative (Ph−) acute lymphoblastic leukemia (ALL), Hodgkin's disease, neuroblastoma, and small cell lung cancer:

Dose of 2.25 mg/m² intravenously over 1 hour once every 7 days.

Vinorelbine has the following structure:

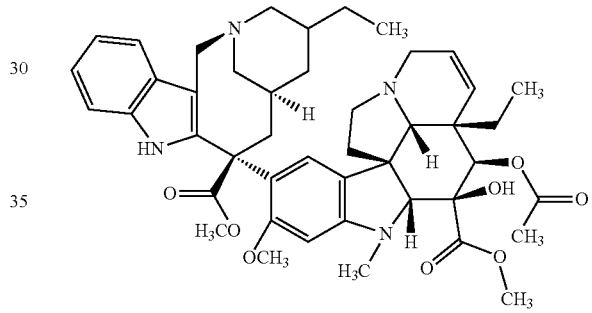

Exemplary dose regimens for vinorelbine in treatment of breast cancer and non-small cell lung cancer include the following:

In combination with cisplatin: 25 to 30 mg/m² as a single intravenous injection weekly.

Single agent: 30 mg/m² as a single intravenous injection weekly.

In addition to the above-described chemotherapeutic drugs, it is expressly contemplated that tepoxalin and/or tepoxalin metabolites or derivatives can also be employed in combination therapy with other cancer therapy methods and compounds, including in combination with chemotherapeutic drugs that do not promote ABCB1-mediated resistance to such chemotherapeutics.

Administration of a composition of the present disclosure to a subject will follow general protocols for the administration described herein, and the general protocols for the administration of a particular secondary therapy will also be followed, taking into account the toxicity, if any, of the treatment. It is expected that the treatment cycles would be repeated as necessary. It also is contemplated that various standard therapies may be applied in combination with the described therapies.

Pharmaceutical Compositions

Agents of the present disclosure can be incorporated into a variety of formulations for therapeutic use (e.g., by administration) or in the manufacture of a medicament (e.g., for treating or preventing cancer, e.g., a cancer that is chemotherapeutic drug resistant and/or expresses high levels of ABCB1) by combining the agents with appropriate pharmaceutically acceptable carriers or diluents, and may be formulated into preparations in solid, semi-solid, liquid or gaseous forms. Examples of such formulations include, without limitation, tablets, capsules, powders, granules, ointments, solutions, suppositories, injections, inhalants, gels, microspheres, and aerosols.

Pharmaceutical compositions can include, depending on the formulation desired, pharmaceutically-acceptable, non-toxic carriers of diluents, which are vehicles commonly used to formulate pharmaceutical compositions for animal or human administration. The diluent is selected so as not to affect the biological activity of the combination. Examples of such diluents include, without limitation, distilled water, buffered water, physiological saline, PBS, Ringer's solution, dextrose solution, and Hank's solution. A pharmaceutical composition or formulation of the present disclosure can further include other carriers, adjuvants, or non-toxic, non-therapeutic, nonimmunogenic stabilizers, excipients and the like. The compositions can also include additional substances to approximate physiological conditions, such as pH adjusting and buffering agents, toxicity adjusting agents, wetting agents and detergents.

Further examples of formulations that are suitable for various types of administration can be found in Remington's Pharmaceutical Sciences, Mace Publishing Company, Philadelphia, PA, 17th ed. (1985). For a brief review of methods for drug delivery, see, Langer, Science 249: 1527-1533 (1990).

For oral administration, the active ingredient can be administered in solid dosage forms, such as capsules, tablets, and powders, or in liquid dosage forms, such as elixirs, syrups, and suspensions. The active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate. Examples of additional inactive ingredients that may be added to provide desirable color, taste, stability, buffering capacity, dispersion or other known desirable features are red iron oxide, silica gel, sodium lauryl sulfate, titanium dioxide, and edible white ink.

Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts of amines, carboxylic acids, and other types of compounds, are well known in the art. For example, S. M. Berge, et al. describe pharmaceutically acceptable salts in detail in J Pharmaceutical Sciences 66 (1977):1-19, incorporated herein by reference. The salts can be prepared in situ during the final isolation and purification of the compounds of the application, or separately by reacting a free base or free acid function with a suitable reagent, as described generally below. For example, a free base function can be reacted with a suitable acid. Furthermore, where the compounds to be administered of the application carry an acidic moiety, suitable pharmaceutically acceptable salts thereof may, include metal salts such as alkali metal salts, e.g. sodium or potassium salts; and alkaline earth metal salts, e.g. calcium or magnesium salts. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Additionally, as used herein, the term "pharmaceutically acceptable ester" refers to esters that hydrolyze in vivo and include those that break down readily in the human body to leave the parent compound (e.g., an FDA-approved compound where administered to a human subject) or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

Furthermore, the term "pharmaceutically acceptable prodrugs" as used herein refers to those prodrugs of certain compounds of the present application which are, within the scope of sound medical judgment, suitable for use in contact with the issues of humans and lower animals with undue toxicity, irritation, allergic response, and the like, commensurate with a reasonable benefit/risk ratio, and effective for their intended use, as well as the zwitterionic forms, where possible, of the compounds of the application. The term "prodrug" refers to compounds that are rapidly transformed in vivo to yield the parent compound of an agent of the instant disclosure, for example by hydrolysis in blood. A thorough discussion is provided in T. Higuchi and V. Stella, Prodrugs as Novel Delivery Systems, Vol. 14 of the A.C.S.

Symposium Series, and in Edward B. Roche, ed., Bioreversible Carriers in Drug Design, American Pharmaceutical Association and Pergamon Press, (1987), both of which are incorporated herein by reference.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

Formulations may be optimized for retention and stabilization in a subject and/or tissue of a subject, e.g., to prevent rapid clearance of a formulation by the subject. Stabilization techniques include cross-linking, multimerizing, or linking to groups such as polyethylene glycol, polyacrylamide, neutral protein carriers, etc. in order to achieve an increase in molecular weight.

Other strategies for increasing retention include the entrapment of the agent, such as tepoxalin, a tepoxalin derivative, RWJ20142 or a RWJ20142 derivative, in a biodegradable or bioerodible implant. The rate of release of the therapeutically active agent is controlled by the rate of transport through the polymeric matrix, and the biodegradation of the implant. The transport of drug through the polymer barrier will also be affected by compound solubility, polymer hydrophilicity, extent of polymer cross-linking, expansion of the polymer upon water absorption so as to make the polymer barrier more permeable to the drug, geometry of the implant, and the like. The implants are of dimensions commensurate with the size and shape of the region selected as the site of implantation. Implants may be particles, sheets, patches, plaques, fibers, microcapsules and the like and may be of any size or shape compatible with the selected site of insertion.

The implants may be monolithic, i.e. having the active agent homogenously distributed through the polymeric matrix, or encapsulated, where a reservoir of active agent is encapsulated by the polymeric matrix. The selection of the polymeric composition to be employed will vary with the site of administration, the desired period of treatment, patient tolerance, the nature of the disease to be treated and the like. Characteristics of the polymers will include biodegradability at the site of implantation, compatibility with the agent of interest, ease of encapsulation, a half-life in the physiological environment.

Biodegradable polymeric compositions which may be employed may be organic esters or ethers, which when degraded result in physiologically acceptable degradation products, including the monomers. Anhydrides, amides, orthoesters or the like, by themselves or in combination with other monomers, may find use. The polymers will be condensation polymers. The polymers may be cross-linked or non-cross-linked. Of particular interest are polymers of hydroxyaliphatic carboxylic acids, either homo- or copolymers, and polysaccharides. Included among the polyesters of interest are polymers of D-lactic acid, L-lactic acid, racemic lactic acid, glycolic acid, polycaprolactone, and combinations thereof. By employing the L-lactate or D-lactate, a slowly biodegrading polymer is achieved, while degradation is substantially enhanced with the racemate. Copolymers of glycolic and lactic acid are of particular interest, where the rate of biodegradation is controlled by the ratio of glycolic to lactic acid. The most rapidly degraded copolymer has roughly equal amounts of glycolic and lactic acid, where either homopolymer is more resistant to degradation. The ratio of glycolic acid to lactic acid will also affect the brittleness of in the implant, where a more flexible implant is desirable for larger geometries. Among the polysaccharides of interest are calcium alginate, and functionalized celluloses, particularly carboxymethylcellulose esters characterized by being water insoluble, a molecular weight of about 5 kD to 500 kD, etc. Biodegradable hydrogels may also be employed in the implants of the individual instant disclosure. Hydrogels are typically a copolymer material, characterized by the ability to imbibe a liquid. Exemplary biodegradable hydrogels which may be employed are described in Heller in: Hydrogels in Medicine and Pharmacy, N. A. Peppes ed., Vol. III, CRC Press, Boca Raton, Fla., 1987, pp 137-149.

Pharmaceutical Dosages

Pharmaceutical compositions of the present disclosure containing an agent described herein may be used (e.g., administered to an individual, such as a human individual, in need of treatment with tepoxalin, a tepoxalin derivative, RWJ20142 or a RWJ20142 derivative) in accord with known methods, such as oral administration, intravenous administration as a bolus or by continuous infusion over a period of time, by intramuscular, intraperitoneal, intracerobrospinal, intracranial, intraspinal, subcutaneous, intraarticular, intrasynovial, intrathecal, topical or inhalation routes.

Dosages and desired drug concentration of pharmaceutical compositions of the present disclosure may vary depending on the particular use envisioned. The determination of the appropriate dosage or route of administration is well within the skill of an ordinary artisan. Animal experiments provide reliable guidance for the determination of effective doses for human therapy. Interspecies scaling of effective doses can be performed following the principles described in Mordenti, J. and Chappell, W. "The Use of Interspecies Scaling in Toxicokinetics," In Toxicokinetics and New Drug Development, Yacobi et al., Eds, Pergamon Press, New York 1989, pp. 42-46.

For in vivo administration of any of the agents of the present disclosure, normal dosage amounts may vary from about 10 ng/kg up to about 100 mg/kg of an individual's and/or subject's body weight or more per day, depending upon the route of administration. In some embodiments, the dose amount is about 1 mg/kg/day to 10 mg/kg/day. For repeated administrations over several days or longer, depending on the severity of the disease, disorder, or condition to be treated, the treatment is sustained until a desired suppression of symptoms is achieved.

An effective amount of an agent of the instant disclosure may vary, e.g., from about 0.001 mg/kg to about 1000 mg/kg or more in one or more dose administrations for one or several days (depending on the mode of administration). In certain embodiments, the effective amount per dose varies from about 0.001 mg/kg to about 1000 mg/kg, from about 0.01 mg/kg to about 750 mg/kg, from about 0.1 mg/kg to about 500 mg/kg, from about 1.0 mg/kg to about 250 mg/kg, and from about 10.0 mg/kg to about 150 mg/kg.

An exemplary dosing regimen may include administering an initial dose of an agent of the disclosure of about 200 µg/kg, followed by a weekly maintenance dose of about 100 µg/kg every other week. Other dosage regimens may be useful, depending on the pattern of pharmacokinetic decay that the physician wishes to achieve. For example, dosing an individual from one to twenty-one times a week is contemplated herein. In certain embodiments, dosing ranging from about 3 µg/kg to about 2 mg/kg (such as about 3 µg/kg, about 10 µg/kg, about 30 µg/kg, about 100 µg/kg, about 300 µg/kg, about 1 mg/kg, or about 2 mg/kg) may be used. In certain embodiments, dosing frequency is three times per day, twice per day, once per day, once every other day, once weekly, once every two weeks, once every four weeks, once every five weeks, once every six weeks, once every seven weeks, once every eight weeks, once every nine weeks, once every ten weeks, or once monthly, once every two months, once every three months, or longer. Progress of the therapy is easily monitored by conventional techniques and assays. The dosing regimen, including the agent(s) administered, can vary over time independently of the dose used.

Pharmaceutical compositions described herein can be prepared by any method known in the art of pharmacology. In general, such preparatory methods include the steps of bringing the agent or compound described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, Poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, Germall® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, *Litsea cubeba*, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates described herein with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such as magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of an agent (e.g., tepoxalin, a tepoxalin derivative, RWJ20142 or a RWJ20142 derivative) described herein may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Additionally, the present disclosure contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices. Intradermal compositions can be administered by devices which limit the effective penetration length of a needle into the skin. Alternatively or additionally, conventional syringes can be used in the classical mantoux method of intradermal administration. Jet injection devices which deliver liquid formulations to the dermis via a liquid jet injector and/or via a needle which pierces the stratum corneum and produces a jet which reaches the dermis are suitable. Ballistic powder/particle delivery devices which use compressed gas to accelerate the compound in powder form through the outer layers of the skin to the dermis are suitable.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition described herein can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions described herein formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition described herein. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition described herein can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition described herein can be prepared, packaged, and/or sold in a formulation for ophthalmic administration. Such formulations may, for example, be in the form of eye drops including, for example, a 0.1-1.0% (w/w) solution and/or suspension of the active ingredient in an aqueous or oily liquid carrier or excipient. Such drops may further comprise buffering agents, salts, and/or one or more other of the additional ingredients described herein. Other ophthalmically-administrable formulations which are useful include those which comprise the active ingredient in microcrystalline form and/or in a liposomal preparation. Ear drops and/or eye drops are also contemplated as being within the scope of this disclosure.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Drugs provided herein can be formulated in dosage unit form for ease of administration and uniformity of dosage. It will be understood, however, that the total daily usage of the agents described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The agents and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the agent or pharmaceutical composition described herein is suitable for oral delivery or intravenous injection to a subject.

The exact amount of an agent required to achieve an effective amount will vary from subject to subject, depending, for example, on species, age, and general condition of a subject, severity of the side effects or disorder, identity of the particular agent, mode of administration, and the like. An effective amount may be included in a single dose (e.g., single oral dose) or multiple doses (e.g., multiple oral doses). In certain embodiments, when multiple doses are administered to a subject or applied to a tissue or cell, any two doses of the multiple doses include different or substantially the same amounts of an agent (e.g., tepoxalin, a tepoxalin derivative, RWJ20142 or a RWJ20142 derivative) described herein.

As noted elsewhere herein, a drug of the instant disclosure may be administered via a number of routes of administration, including but not limited to: subcutaneous, intravenous, intrathecal, intramuscular, intranasal, oral, transepidermal, parenteral, by inhalation, or intracerebroventricular.

The term "injection" or "injectable" as used herein refers to a bolus injection (administration of a discrete amount of an agent for raising its concentration in a bodily fluid), slow bolus injection over several minutes, or prolonged infusion, or several consecutive injections/infusions that are given at spaced apart intervals.

In some embodiments of the present disclosure, a formulation as herein defined is administered to the subject by bolus administration.

A drug or other therapy of the instant disclosure is administered to the subject in an amount sufficient to achieve a desired effect at a desired site (e.g., reduction of cancer size, cancer cell abundance, symptoms, etc.) determined by a skilled clinician to be effective. In some embodiments of the disclosure, the agent is administered at least once a year. In other embodiments of the disclosure, the agent is administered at least once a day. In other embodiments of the disclosure, the agent is administered at least once a week. In some embodiments of the disclosure, the agent is administered at least once a month.

Additional exemplary doses for administration of an agent of the disclosure to a subject include, but are not limited to, the following: 1-20 mg/kg/day, 2-15 mg/kg/day, 5-12 mg/kg/day, 10 mg/kg/day, 1-500 mg/kg/day, 2-250 mg/kg/day, 5-150 mg/kg/day, 20-125 mg/kg/day, 50-120 mg/kg/day, 100 mg/kg/day, at least 10 µg/kg/day, at least 100 µg/kg/day, at least 250 µg/kg/day, at least 500 µg/kg/day, at least 1 mg/kg/day, at least 2 mg/kg/day, at least 5 mg/kg/day, at least 10 mg/kg/day, at least 20 mg/kg/day, at least 50 mg/kg/day, at least 75 mg/kg/day, at least 100 mg/kg/day, at least 200 mg/kg/day, at least 500 mg/kg/day, at least 1 g/kg/day, and a therapeutically effective dose that is less than 500 mg/kg/day, less than 200 mg/kg/day, less than 100 mg/kg/day, less than 50 mg/kg/day, less than 20 mg/kg/day, less than 10 mg/kg/day, less than 5 mg/kg/day, less than 2 mg/kg/day, less than 1 mg/kg/day, less than 500 µg/kg/day, and less than 500 µg/kg/day.

In certain embodiments, when multiple doses are administered to a subject or applied to a tissue or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, the frequency of administering the multiple doses to the subject or applying the multiple doses to the tissue or cell is three doses per day. In certain embodiments, when multiple doses are administered to a subject or applied to a tissue or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell. In certain embodiments, a dose (e.g., a single dose, or any dose of multiple doses) described herein includes independently between 0.1 g and 1 g, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of an agent (e.g., tepoxalin, a tepoxalin derivative, RWJ20142 or a RWJ20142 derivative) described herein. In certain embodiments, a dose described herein includes independently between 1 mg and 3 mg, inclusive, of an agent (e.g., tepoxalin, a tepoxalin derivative, RWJ20142 or a RWJ20142 derivative) described herein. In certain embodiments, a dose described herein includes independently between 3 mg and 10 mg, inclusive, of an agent (e.g., tepoxalin, a tepoxalin derivative, RWJ20142 or a RWJ20142 derivative) described herein. In certain embodiments, a dose described herein includes independently between 10 mg and 30 mg, inclusive, of an agent (e.g., tepoxalin, a tepoxalin derivative, RWJ20142 or a RWJ20142 derivative) described herein. In certain embodiments, a dose described herein includes independently between 30 mg and 100 mg, inclusive, of an agent (e.g., tepoxalin, a tepoxalin derivative, RWJ20142 or a RWJ20142 derivative) described herein.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult. In certain embodiments, a dose described herein is a dose to an adult human whose body weight is 70 kg.

It will be also appreciated that an agent (e.g., tepoxalin, a tepoxalin derivative, RWJ20142 or a RWJ20142 derivative) or composition, as described herein, can be administered in combination with one or more additional pharmaceutical agents (e.g., therapeutically and/or prophylactically active agents), which are different from the agent or composition and may be useful as, e.g., combination therapies.

The agents or compositions can be administered in combination with additional pharmaceutical agents that improve their activity (e.g., activity (e.g., potency and/or efficacy) in treating a disease (e.g., cancer) in a subject in need thereof, in preventing a disease in a subject in need thereof, in reducing the risk of developing a disease in a subject in need thereof, etc. in a subject or cell. In certain embodiments, a pharmaceutical composition described herein including an agent (e.g., tepoxalin, a tepoxalin derivative, RWJ20142 or a RWJ20142 derivative) described herein and an additional pharmaceutical agent shows a synergistic effect that is absent in a pharmaceutical composition including one of the agent and the additional pharmaceutical agent, but not both.

In some embodiments of the disclosure, a therapeutic agent distinct from a first therapeutic agent of the disclosure is administered prior to, in combination with, at the same time, or after administration of the agent of the disclosure. In some embodiments, the second therapeutic agent is selected from the group consisting of a chemotherapeutic, an immunotherapy, an antioxidant, an antiinflammatory agent, an antimicrobial, a steroid, etc.

The agent or composition can be administered concurrently with, prior to, or subsequent to one or more additional pharmaceutical agents, which may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease described herein. Each additional pharmaceutical agent may be administered at a dose and/or on a time schedule determined for that pharmaceutical agent. The additional pharmaceutical agents may also be administered together with each other and/or with the agent or composition described herein in a single dose or administered separately in different doses. The particular combination to employ in a regimen will take into account compatibility of the agent described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

The additional pharmaceutical agents include, but are not limited to, additional tepoxalin derivatives, RWJ20142 or RWJ20142 derivatives, other anti-cancer agents, immunotherapy and/or immunomodulatory agents, anti-proliferative agents, cytotoxic agents, anti-angiogenesis agents, anti-inflammatory agents, immunosuppressants, anti-bacterial agents, anti-viral agents, cardiovascular agents, cholesterol-lowering agents, anti-diabetic agents, anti-allergic agents, contraceptive agents, and pain-relieving agents. In certain embodiments, the additional pharmaceutical agent is an anti-proliferative agent. In certain embodiments, the additional pharmaceutical agent is an anti-cancer agent. In certain embodiments, the additional pharmaceutical agent is an anti-viral agent. In certain embodiments, the additional pharmaceutical agent is selected from the group consisting of epigenetic or transcriptional modulators (e.g., DNA methyltransferase inhibitors, histone deacetylase inhibitors (HDAC inhibitors), lysine methyltransferase inhibitors), antimitotic drugs (e.g., taxanes and vinca alkaloids), hormone receptor modulators (e.g., estrogen receptor modulators and androgen receptor modulators), cell signaling pathway inhibitors (e.g., tyrosine kinase inhibitors), modulators of protein stability (e.g., proteasome inhibitors), Hsp90 inhibitors, glucocorticoids, all-trans retinoic acids, and other agents that promote differentiation. In certain embodiments, the agents described herein or pharmaceutical compositions can be administered in combination with an anti-cancer therapy including, but not limited to, surgery, radiation therapy, transplantation (e.g., stem cell transplantation, bone marrow transplantation), immunotherapy, and chemotherapy.

Dosages for a particular agent of the instant disclosure may be determined empirically in individuals who have been given one or more administrations of the agent.

Administration of an agent of the present disclosure can be continuous or intermittent, depending, for example, on the recipient's physiological condition, whether the purpose of the administration is therapeutic or prophylactic, and other factors known to skilled practitioners. The administration of an agent may be essentially continuous over a preselected period of time or may be in a series of spaced doses.

Guidance regarding particular dosages and methods of delivery is provided in the literature; see, for example, U.S. Pat. No. 4,657,760; 5,206,344; or 5,225,212. It is within the scope of the instant disclosure that different formulations will be effective for different treatments and different disorders, and that administration intended to treat a specific organ or tissue may necessitate delivery in a manner different from that to another organ or tissue. Moreover, dosages may be administered by one or more separate administrations, or by continuous infusion. For repeated administrations over several days or longer, depending on the condition, the treatment is sustained until a desired suppression of disease symptoms occurs. However, other dosage regimens may be useful. The progress of this therapy is easily monitored by conventional techniques and assays.

Kits

The instant disclosure also provides kits containing agents of this disclosure for use in the methods of the present disclosure. Kits of the instant disclosure may include one or more containers comprising an agent (e.g., tepoxalin, a tepoxalin derivative, RWJ20142 or a RWJ20142 derivative) of this disclosure and/or may contain agents (e.g., oligonucleotide primers, probes, etc.) for identifying a cancer or subject as chemotherapeutic resistant and/or as exhibiting elevated ABCB1 levels. In some embodiments, the kits further include instructions for use in accordance with the methods of this disclosure. In some embodiments, these instructions comprise a description of administration of the agent to treat or diagnose, e.g., a cancer that exhibits elevated expression of ABCB1 and/or amplification of the ABCB1 locus, according to any of the methods of this disclosure. In some embodiments, the instructions comprise a description of how to detect a cancer or subject as chemotherapeutic resistant and/or as exhibiting elevated ABCB1 levels, for example in an individual, in a tissue sample, or in a cell. The kit may further comprise a description of selecting an individual suitable for treatment based on identifying whether that subject has a cancer that is chemotherapeutic resistant and/or as exhibits elevated ABCB1 levels.

The instructions generally include information as to dosage, dosing schedule, and route of administration for the intended treatment. The containers may be unit doses, bulk packages (e.g., multi-dose packages) or sub-unit doses. Instructions supplied in the kits of the instant disclosure are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, e.g., a cancer or subject as chemotherapeutic drug resistant and/or as exhibiting elevated ABCB1 levels, in a subject. Instructions may be provided for practicing any of the methods described herein.

The kits of this disclosure are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (e.g., the container may be an intravenous solution bag or a vial having a stopper pierceable by a hypodermic injection needle). In certain embodiments, at least one active agent in the composition is tepoxalin, a tepoxalin derivative, RWJ20142 or a RWJ20142 derivative. The container may further comprise a second pharmaceutically active agent.

Kits may optionally provide additional components such as buffers and interpretive information. Normally, the kit comprises a container and a label or package insert(s) on or associated with the container.

The practice of the present disclosure employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, Molecular Cloning (Cold Spring Harbor Laboratory Press, Cold Spring Harbor, N.Y.); Sambrook et al., 1989, Molecular Cloning, 2nd Ed. (Cold Spring Harbor Laboratory Press, Cold Spring Harbor, N.Y.); Sambrook and Russell, 2001, Molecular Cloning, 3rd Ed. (Cold Spring Harbor Laboratory Press, Cold Spring Harbor, N.Y.); Ausubel et al., 1992), Current Protocols in Molecular Biology (John Wiley & Sons, including periodic updates); Glover, 1985, DNA Cloning (IRL Press, Oxford); Anand, 1992; Guthrie and Fink, 1991; Harlow and Lane, 1988, Antibodies, (Cold Spring Harbor Laboratory Press, Cold Spring Harbor, N.Y.); Jakoby and Pastan, 1979; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Riott, Essential Immunology, 6th Edition, Blackwell Scientific Publications, Oxford, 1988; Hogan et al., Manipulating the Mouse Embryo, (Cold Spring Harbor Laboratory Press, Cold Spring Harbor, N.Y., 1986); Westerfield, M., The zebrafish book. A guide for the laboratory use of zebrafish (*Danio rerio*), (4th Ed., Univ. of Oregon Press, Eugene, 2000).

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Reference will now be made in detail to exemplary embodiments of the disclosure. While the disclosure will be described in conjunction with the exemplary embodiments, it will be understood that it is not intended to limit the disclosure to those embodiments. To the contrary, it is intended to cover alternatives, modifications, and equivalents as may be included within the spirit and scope of the disclosure as defined by the appended claims. Standard techniques well known in the art or the techniques specifically described below were utilized.

EXAMPLES

Example 1: Materials and Methods

PRISM Screening

Parental cell lines were obtained from the Cancer Cell Line Encyclopedia (CCLE) project (4). PRISM cell line barcoding, pooling, and screening was performed as previously described with several improvements to the original method (5). First, the lentiviral vector was modified to encode the unique barcode identifier at the end of the puromycin resistance gene. This enables barcodes to be detected using a variant of the mRNA capture and Luminex detection method developed for the L1000 gene expression assay (6). Second, a set of ten inert barcodes were spiked-in to each well of each plate after cell lysis to control for variation in PCR amplification as detailed below.

Data Processing

Luminex technology produced .lxb files containing data for each Luminex bead observed during detection. These .lxb files were processed to compute Median Fluorescence Intensity (MFI) values, calculated as the median of the values obtained for all beads corresponding to a single PRISM barcode.

MFI values were log-transformed (log MFI) and used to perform basic quality control. To detect probable screening artifacts, log MFI values were centered to the median log MFI for each cell line on each plate in order to put the measurements from each cell line on the same scale. For each well on each plate, the median of these centered values was then standardized according to the global median and global MAD across all plate wells in the same position. Data from wells with a standardized score of greater than 5 or less than −5 were excluded from all further processing steps.

For each cell line on each plate, the distribution of MFI values observed for the DMSO-treated negative controls was compared to that of the positive controls using a robust form of the Strictly Standardized Mean Difference (SSMD*)'. Specifically, SSMD* was calculated as:

$$\frac{(\mu_- - \mu_+)}{\sqrt{\sigma_-^2 + \sigma_+^2}}$$

Data corresponding to SSMD values less than 2 were removed before calculating cell viability.

The data in the instant disclosure were produced according to two different screening protocols. In the PR500 protocol, ten inert barcodes were spiked-in to each well of each plate after cell lysis. For data produced using the PR500 protocol, normalized MFI (nMFI) values were computed by taking the ratio of each MFI value against the median of the inert barcodes within each well. For data produced before the PR500 protocol was introduced, nMFI values were set equal to MFI values.

Cell viability was calculated as the ratio of nMFI to the median of the nMFI from the DMSO-treated negative controls for each cell line on each plate. Batch effects produced from variable detection and assay conditions were then removed using ComBat (8). The final viability values were calculated as the median of the batch-corrected cell viabilities from biological replicates for each cell line, compound and dose.

Dose Response

Measures of dose response were obtained by fitting 3-parameter logistic curves to viability values for each compound and cell line using the R package 'drc'. Following the practice of Smirnov and Safikhani (9), viability was truncated at 1.0 and fit as a function of drug concentration according to:

$$V(c) = E_\infty + \frac{1 - E_\infty}{1 + e^{HS(c - EC50)}}$$

where all concentrations are in the natural logarithm scale. IC50 values were defined as the concentration c at which V(c)=0.5, given by the formula:

$$IC50 = -\frac{\log(1 - 2E_\infty)}{HS} + EC50$$

The Area Under the dose response Curve (AUC) was calculated using the normalized integral:

$$\frac{\int_{c_{min}}^{c_{max}} V(c)dc}{c_{max} - c_{min}}$$

where $$\int V(c)dc = \frac{(E_\infty - 1)\log(1 + e^{-HS(c-EC50)})}{HS} + E_\infty c + const$$

The formulation above puts AUC values on a scale between 0 and 1, where lower AUC values indicate increased sensitivity to the treatment.

Nomination for Secondary Screen

Compounds from the primary screen were labeled as candidates for secondary screening using a combination of cell killing metrics and goodness-of-fit measures obtained from the ATLANTIS method (10). Metrics considered were profile mean, variance, skewness, number of sensitive cell lines as well as the 75th, 25th, 10th and 5th quantiles of each profile's distribution. Cell lines were defined as sensitive to a compound if their median log fold change after batch correction was below 2 standard deviations of the distribution of DMSO controls. ATLANTIS model R2 values of above 0.1 were considered strong models. Subject to compound availability and manual curation, candidates were progressed to secondary profiling at 8 point dose.

Antibodies and Reagents

Elacridar (#57772), Paclitaxel (#S1150), and Doxorubicin (#S1208) were purchased from Selleck Chemicals. DMSO was purchased from Sigma-Aldrich. Tepoxalin (#T103205) was purchased from Toronto Research Chemicals. MDR1/ABCB1 (D3H1Q) Rabbit mAb (#12683), MDR1/ABCB1 (E1Y7B) Rabbit mAb (#13342S), I3-Actin (8H10D10) Mouse mAb (#3700S), and were purchased from cell signaling.

Cell Lines

LS1034 and HEK293 cells were purchased from the American Type Culture Collection. REC1, JHH7, BEN, RCC10ORGB, and COL0320 were provided by the Broad-Novartis Cancer Cell Line Encyclopedia. pLx_317_ABCB1 and parental lines for OVCAR4 and Kuramochi were gifts from Elizabeth Stover. LS1034, REC1, COL0320, and JHH7 cell lines derived with Cas9 were provided by the Broad Cancer Dependency Map. LS1024, REC1, RCC1OORGB, OVCAR4, COL0320, and Kuramochi cell lines were cultured in RPM! (Thermo #11875093), JHH7 cells were cultured in McCoy5A (Thermo #16600082). BEN cell line were culture using DMEM (Thermo #10566016). All media was supplemented with 10% heat inactivated serum PBS (Sigma 18A079) and 1% penicillin-streptomycin G (Thermo #10378016) except for the HEK293 which was maintained without antibiotics.

RNAseq gene expression data was obtained from the CCLE website (portals.broadinstitute.org/ccle). Identity of all human cell lines was confirmed by STR fingerprinting (Genetica).

Cloning

XP003, XP023, psPAX, and pMD2.G vectors were acquired from the Broad Genetic Perturbation Platform (GPP). Oligos for sgRNAs designs were generated using Broad GPP sgRNA guide generator resource (www.broadinstitute.org/gpp/db/analysis-tools/sgrna-design) and the respective oligos were synthesized by Integrated DNA Technologies. In order to clone the sgRNAs into either the XPR003 guide only or XPRO23 all-in-one crispr lentiviral expression systems the protocol available on the Broad GPP website (www.broadinstitute.org/gpp/db/resources/protocols) was followed.

Viral Vector Generation

In order to generate viral vectors, HEK293T cells were seeded in 6 well plates at a density of 1.5E6 cells per well. Cells were then transfected with a mixture of TransIT®-LT1 Transfection Reagent (MirusBio #M1R2304), psPAX2, pMD2.G, lentiviral plasmid diluted in Opti-MEM™ (Thermo #31985062). The following day media was changed DMEM (Thermo #10566016) with 30% FBS (Sigma 18A079). 72 hrs after transfection, virus containing media was collected and run through a 0.2 uM filter to remove cellular debris. Virus was aliquoted and stored short term at −20 C until infection day.

Lentiviral Infection

A mixture of 3E6 cells, virus, and media with 4 µg/mL polybrene (Millipore) at a total volume of 2 mL was plated per well of a 12 well plate. Cells were centrifuged at 2000 RPM for 2 hours at 30° C. After removal from incubator, 2 mL of fresh media was added to each well and cells were allowed to incubate at 37° C. overnight. The following day cells were selected for with puromycin for 3-10 days, or until the non-infected control cell were completely non-viable.

CellTiter-Glo® Cellular Viability Assay

Cell viability was assayed using a modified manufacturer's protocol for CellTiter-Glo® (Promega #G7573). Cells were seeded at a density of 2000 cells per well in a 96 well black, clear bottom plate (Corning #89091-012) in 100 uL total media per well. The following day different concentrations of compounds at various doses were printed in triplicate in a random well format using the Tecan D300e Digital Dispenser. After 120H, 60 µL of a 1:3 solution of CellTiterGlo reagent in 1×PBS (Corning #01018002) was added per well and allowed to incubate at RT for 10 mins. Luminescence was measured with an integration time of 0.1 s using Envision Microplates Reader (PERKIN ELMER #2105-0010). Biological replicates were averaged and normalized to vehicle control. Dose curves were generated using Graphpad Prism.

Western Immunoblotting

Adherent cells were washed once with cold lx PBS (Corning #01018002) and lysed with RIPA buffer (Sigma #R0278) supplemented by protease and phosphatase inhibitors (Sigma). Protein content was quantified using the DC Protein Assay (BioRad #5000111). Samples were reduced with (loading buffer) and boiled at 95° C. before being resolved by SDS gel electrophoresis on 4-20% Tris/glycine gels (Invitrogen). Proteins were transferred using the IBlot2 (Thermo #IB21001) onto the iBlot™ 2 nitrocellulose Transfer Stacks (Thermo #IB23001). The membranes were then blocked in Odyssey Blocking Buffer (Li-COR #927-40000) for one hour, and then probed overnight with primary antibodies diluted in blocking buffer. The following day, membranes were washed 3×5 mins with 1×TBST and then probed with LiCOR Infrared secondary antibodies for 1 hour at room temperature. Membranes were washed an additional 3×5 mins in 1×TBST and then imaged using the LiCOR Imager.

CRISPR Genome-Wide Knockout Modifier Screen

Pooled Brunello library virus was acquired from the Broad institute Genetic Perturbation Platform. The virus was titrated to achieve an infection MOI of 0.3-0.6. 400 million Cas9-derivatized LS1034 cells were infected with the Brunello virus library which contains 76,441 sgRNAs and 1000 control sgRNAs targeting 19,114 genes (11). The following day cells were trypsinized and split into two biological replicates and selected for with 6 µg/mL puromycin for 7 days. After selection, replicates were seeded into a drug arm of either 4 µM, 8 µM, 16 µM tepoxalin (Wuxi) or DMSO control. Cells were maintained at 37 C and 5% $CO_2$ in CelISTACK 1272 cm2 2-STACK flasks (Corning #3269) in RPMI with 10% FBS. Cells were trypsinized and reseeded every 7 days at a bottleneck of 40 million cells in order to maintain library representation. Media and tepoxalin was refreshed every 3-4 days. Cell pellets were harvested after before the addition of drug and every passage up to 30 days of drug treatment. Genomic DNA was isolated from cell pellets using the NucleoSpin® Blood XL Columns (Machery Nagel #740950.50) following the manufacturer's protocol. Genomic DNA sequencing and analysis was performed by the Broad Genetic Perturbation Platform protocol using standard protocols.

CRISPR Genome-Wide Activation Screen

LS1034 cells were first derivatized with XPR109, which encodes dCas9-VP64. XPR502, which encodes PP7-P65-HSF and a sgRNA tracr with two MS2 loops and two PP7 loops. Transcriptional activator functionality was confirmed by infecting derivatized cells with sgRNAs targeting CD4 and CD45 and observing an increase in CD4 and CD45-positive cells with flow cytometry. For the screen, cells were infected with the Calabrese B virus library, and following selection with puromycin, split into DMSO or 16 uM tepoxalin drug arms in duplicate and cultured for 2 weeks. Multiplicity of infection (M01) was calculated to be . . . . Genomic DNA was harvested and sequenced as described above.

Brunello and Calabrese CRISPR guide virus libraries with obtained from the Broad Genomic Perturbation Platform. The XPRO03, XPRO23, XPR109, and XPR311 vectors were gifts of John Doench and David Root.

Tepoxalin Blood Measurement

Serum/plasma samples were thawed on ice and a 50 pL aliquot was precipitated with 3 volumes of acetonitrile (Honeywell, catalog #34967-4X4L) containing internal standard (75 nM midazolam, Acme Biosciences, catalog #A5020). Following centrifugation at 3000×g for 15 minutes at 20° C., a 100 pL aliquot of the supernatant was removed and diluted with a matching volume of water (JT Baker, catalog #9831-03). Samples were analyzed on a UPLC-MS/MS system consisting of a Waters Acquity I-Class FTN and AB Sciex 4500 Triple Quad mass spectrometer with compounds being detected by positive mode MRM detection. Mobile phase A consisted of water with 0.1% formic acid (Honeywell, catalog #33015-1L), while mobile phase B consisted of acetonitrile with 0.1% formic acid. The gradient ran from 10-95% B over 0.8 minutes at a flow rate of 0.9 mL/minute. An Acquity BEH C18, 1.7 m, 2.1×50 mm column (Waters, P/N 186002350) was used with column temperature maintained at 65° C. Sample concentrations were determined using a standard curve and dilution quality control samples prepared in a surrogate matrix. Analyst 1.6.2 software was used for integration and calculation determination.

Compound Cell Permeability Assay

Compound was incubated in naïve cell media (no cell control, or NCC) or in the presence of cells at 1 million cells/mL. The incubation was carried out in a 37° C. with 5% $CO_2$ cell incubator with gentle plate shaking for 3 hours. Following the incubation, the NCC samples were placed on the bench until final analysis. Cell samples were centrifuged at 500×g for 5 minutes. The supernatant was removed, and the cells were washed twice with cold PBS. Cells were again centrifuged at 500×g for 5 minutes, the supernatant was removed/discarded, and cells were resuspended in 130 pL water (Honeywell, catalog #33015-1L). The entire volume was then transferred into a Covaris microTUBE plate (Covaris, catalog #220078) and sonicated on a Covaris LE220 focused-ultrasonicator. Samples were transferred to a 96wp and centrifuged at 3000×g for 15 min at 20° C. The supernatant was transferred to a new 96wp. For both the NCC and cell samples, 5 pL was transferred to a 96wp. To each sample was added 45 pL cell media, 50 pL water, and 50 pL acetonitrile containing internal standard. Samples were centrifuged again, and a final 100 pL aliquot was transferred to a 96wp for analysis.

Samples were analyzed on a UPLC-MS/MS system consisting of a Waters Acquity I-Class FTN and AB Sciex 4500 Triple Quad mass spectrometer with compounds being detected by positive mode MRM detection. Mobile phase A consisted of water with 0.1% formic acid (Honeywell, catalog #33015-1L), while mobile phase B consisted of acetonitrile with 0.1% formic acid. The gradient ran from 10-95% B over 0.8 minutes at a flow rate of 0.9 mL/minute. An Acquity BEM C18, 1.7 m, 2.1×50 mm column (Waters, P/N 186002350) was used with column temperature maintained at 65° C. Sample concentrations were determined using a standard curve and dilution quality control samples prepared in a surrogate matrix. Analyst 1.6.2 software was used for integration and calculation determination.

P-Glycoprotein Transporter Cell Based Antagonism Assay

P-Glycoprotein antagonism assay for Tepoxalin and RWJ20142 was performed by Europhins using their standard protocols. In brief, MDCKII cMDR1 KO with and without overexpression of hMDR1 were at several doses with compound or known ABCB1 inhibitor verapamil for 2 hours_Calcein AM, MDR1 substrate and cell permeable dye that is activated to its fluorescent form upon entering the cell, was added for min/hours.

Cyprotex MDKII MDR1 Monolayer Assay

MDKII cell monolayer assay was performed by Cyprotex following standard protocols. Tepoxalin was screened at dose and compared verapamil positive control compound.

Example 2: High-Throughput Cytotoxicity Profiling of a Drug Repurposing Library Revealed Tepoxalin as a Compound Possessing Selectivity for Killing of ABCB1 Overexpressing Cell Lines A drug repurposing library (described in Corsello et al. *Nat. Medicine* 23: 405-408) was employed to investigate whether any existing therapeutic could be identified that showed efficacy in combatting the development of chemotherapeutic resistance in targeted cancer cell lines (the rationale for using a drug repurposing library being that clinical development of an existing therapeutic identified to show such an effect could be performed more rapidly and at lower cost than de novo drug development). The Corsello et al. drug repurposing library includes approximately 2000 compounds that have achieved launch, approximately 400-600 drugs, respectively, that have each advanced to phases 1, 2 or 3 clinical trials, a limited number of drugs that have been withdrawn from such trials and/or release (less than 100) and approximately 1300 drugs that are in preclinical/discovery phases of drug development.

Specifically, for the instant disclosure, the above-described drug repurposing library was assayed to identify any component compounds that exhibited efficacy against cells possessing chemotherapeutic resistance conferred by elevated expression of ABCB1 (also known as MDR1, p-glycoprotein), in view of previous description of ABCB1 as a pump that possesses the ability to transport many different chemotherapy and targeted therapy drugs, thereby rendering tumors resistant to such therapies. Accordingly, the arrayed drug repurposing library was applied to pooled, barcode-tagged neoplastic cell line populations (see Yu et al. *Nature Biotechnology* 34: 419-423, which describes a cell line barcoding and pooling approach by which the relative expansion or contraction of individual barcoded cell lines within a cell line population (i.e., 800+ cell lines derived from 23 lineages) can be monitored during high-throughput application in parallel of hundreds to thousands of individual compounds from an arrayed library). High-throughput "next gen" sequencing performed upon arrayed cell populations allowed for well-by-well tracking of cell viability over time, in the presence and absence of library compounds, via barcode enumeration and deconvolution of treated and control cell line populations. Using this approach, cell viability dose-response curves were generated for each compound of the drug repurposing library, across all targeted cell lines present in the barcode-tagged neoplastic cell line "PRISM" populations.

The expression of metabolic enzymes or drug efflux pumps were among the most commonly discovered predictive biomarkers of drug response in the "PRISM" screen. For example, high mRNA expression of the ABCB1 transporter (MDR1/p-glycoprotein) was the top predictor of resistance to numerous approved cancer therapeutics including taxanes (docetaxel and paclitaxel), anthracyclines (daunorubicin, doxorubicin, and epirubicin), vinca alkaloids (vincristine and vinorelbine), and proteasome inhibitors (carlifizomib).

Figure 1B:
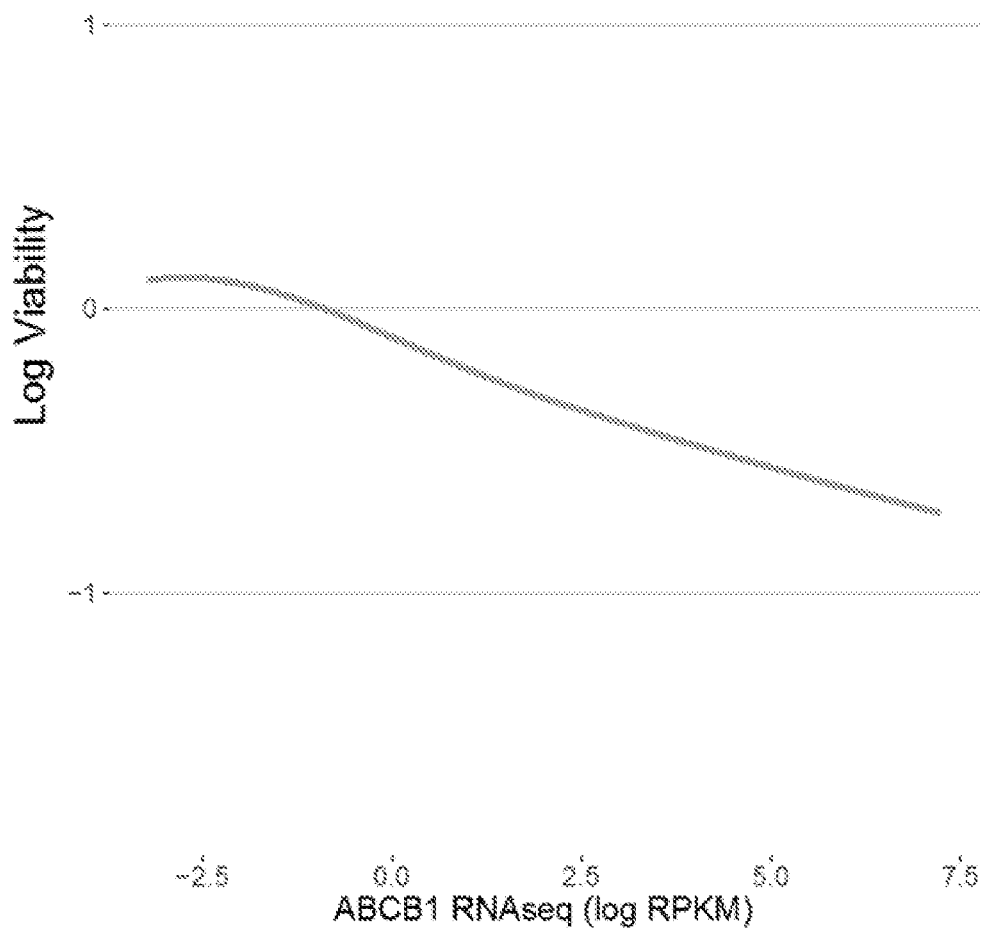
Figure 2:
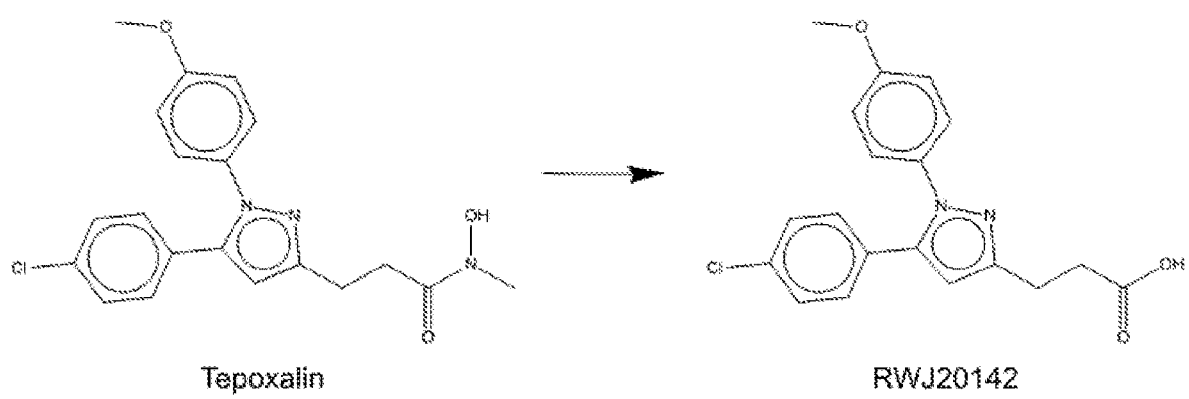
FIG. 2 shows the tepoxalin compound and its active metabolite, RWJ20142. Tepoxalin is FDA approved for treatment of osteoarthritis in dogs (the compound reached phase II human trials for osteoarthritis). Tepoxalin has been identified as safe and effective for pain relief in dogs and has been described to function as a dual inhibitor of cyclooxygenase and 5-lipoxygenase. In vivo metabolism of the hydroxamic acid moiety of tepoxalin has been identified to yield RWJ20142 as an active metabolite.

By sorting the "PRISM" population cell lines by their respective relative levels of ABCB1 expression (as assessed by RNAseq), the cell killing profile of each drug repurposing library compound tested could be plotted against relative levels of ABCB1 expression, thereby obtaining a cell killing profile that served as a proxy for dose-response of the library compound across progressively increasing levels of ABCB1 expression. Consistent with ABCB1's established role in imparting chemotherapeutic drug resistance to neoplasia cell lines, docetaxel and a number of other known chemotherapeutic drugs (i.e., busulfan, carfilzomib, daunorubicin, doxorubicin, epirubicin, idarubicin, ixabepilone, paclitaxel, romidepsin, vincristine and vinorelbine) exhibited robust killing of cells that expressed low levels of ABCB1, yet increased expression of ABCB1 in cell lines administered docetaxel and the various other known chemotherapeutic drugs resulted tended to block chemotherapeutic-mediated cell killing (FIG. 1A). Remarkably, tepoxalin, an FDA-approved drug for treatment of osteoarthritis in dogs, exhibited progressively enhanced killing of cell lines in positive correlation with increasing levels of ABCB1 in the PRISM population of assayed cell lines—thus, high ABCB1 expression predicted sensitivity to tepoxalin (FIG. 1). It was contemplated that such a pattern of selective activity would likely be useful in treating patients with chemotherapy-resistant cancers. Tepoxalin is a veterinary drug that is FDA-approved for treatment of osteoarthritis in dogs. It is an orally administered dual inhibitor of cyclooxygenase and 5-lipoxygenase (1). An effective dose of tepoxalin was found to produce fewer gastric ulcers in a rat model than naproxen. Tepoxalin possesses a hydroxamic acid moiety that is metabolized in vivo to produce an active metabolite, RWJ20142 (FIG. 2).

Various individual neoplasia cell lines that possess increased ABCB1 expression were also identified to be highly sensitive to tepoxalin—specific examples of such cell lines included lung, large intestine, bone, ovary, kidney, liver, biliary tract and thyroid cancer cell lines (FIG. 3).

Next, whether tepoxalin's activity was likely to be on- or off-target was investigated. The cell killing (anti-cancer) activity of tepoxalin was likely driven by an off-target effect, as more than 100 other types of cyclooxygenase or lipoxygenase inhibitors present in the "PRISM"-assayed compound repurposing library were observed not to possess similar activity as tepoxalin (such compounds were observed to be inactive for such effect and these other compounds exhibited distinct activity profiles from tepoxalin). Moreover, there was no observed tepoxalin correlation with genetic dependency on COX1, COX2 or 5-lipoxygenase (which would have been predicted for on-target cyclooxygenase or lipoxygenase inhibitory effects)—tepoxalin's activity did not correlate with cell line genetic knockout profiles for PTGS1, PTGS2, or ALOX5. Tepoxalin also did not phenocopy other known ABCB1 inhibitors. Potent ABCB1 small molecule inhibitors such as elacridar, tariquidar, and zosuquidar did not phenocopy tepoxalin in "PRISM" when tested at the same dose. Thus, tepoxalin was identified as likely active against ABCB1-high cancer cell lines via a novel mechanism.

Figure 4:
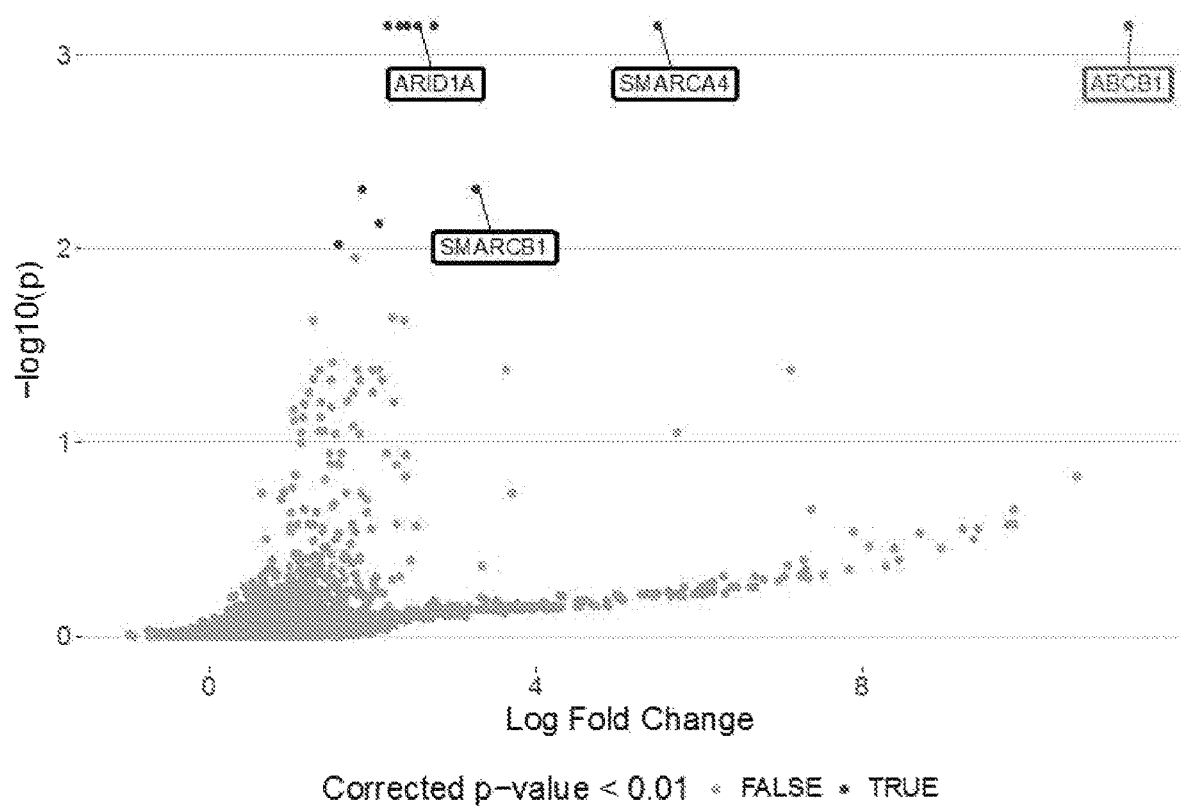
FIG. 4 shows the results of a genome-wide CRISPR modifier screen that demonstrated rescue of cells from tepoxalin-mediated cell killing by knockout of the ABCB1 (MDR1) transporter (ABCB1 knockout therefore inhibited/blocked tepoxalin-mediated cell killing).

To elucidate genes required for topaxalin cytotoxicity, a pooled, genome-wide CRISPR-Cas9 modifier screen was performed. LS1034 colorectal cancer cells with high expression of ABCB1 at baseline were infected with a pooled Brunello guide library containing 76,441 gRNAs targeting 19,114 genes. Following infection and puromycin selection, cells were treated in duplicate at 3 doses of tepoxalin for 30 days. Genomic DNA was isolated and guide abundance was determine by next-generation (next-gen) sequencing (NGS). The top gene positively enriched for resistance was ABCB1 itself (FIG. 4; guides ranked 1-4 at the top dose). Other resistance hits included multiple components of the SWI/SNF complex (SMARA4, SMARCBI, and ARID1A), which has been previously implicated in regulation of ABCB1 gene expression (2). Individual knockout of ABCB1 reduced tepoxalin sensitivity in multiple colorectal cancer cell lines including LS1034, COL0320, and SNU441. Thus, it was identified that a targeted cell's tepoxalin sensitivity could be rescued via knockout of ABCB1 (FIG. 4).

Figure 5A:
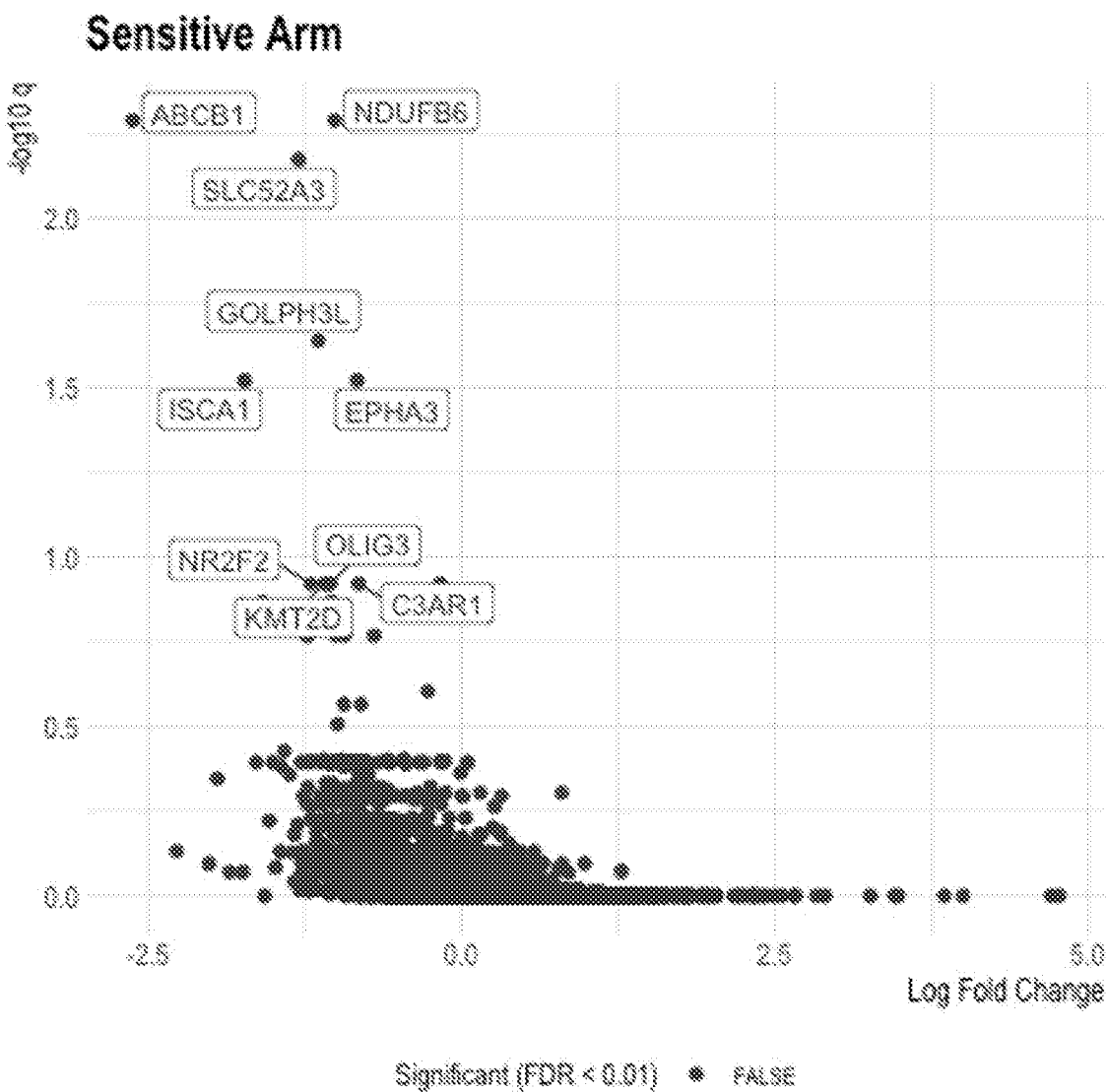
FIGS. 5A and 5B show the results of a genome-wide CRISPR activation screen that demonstrated that overexpression of ABCB1 (MDR1) increased the sensitivity of cells to tepoxalin (tepoxalin-mediated cell killing was enhanced).
Figure 5B:
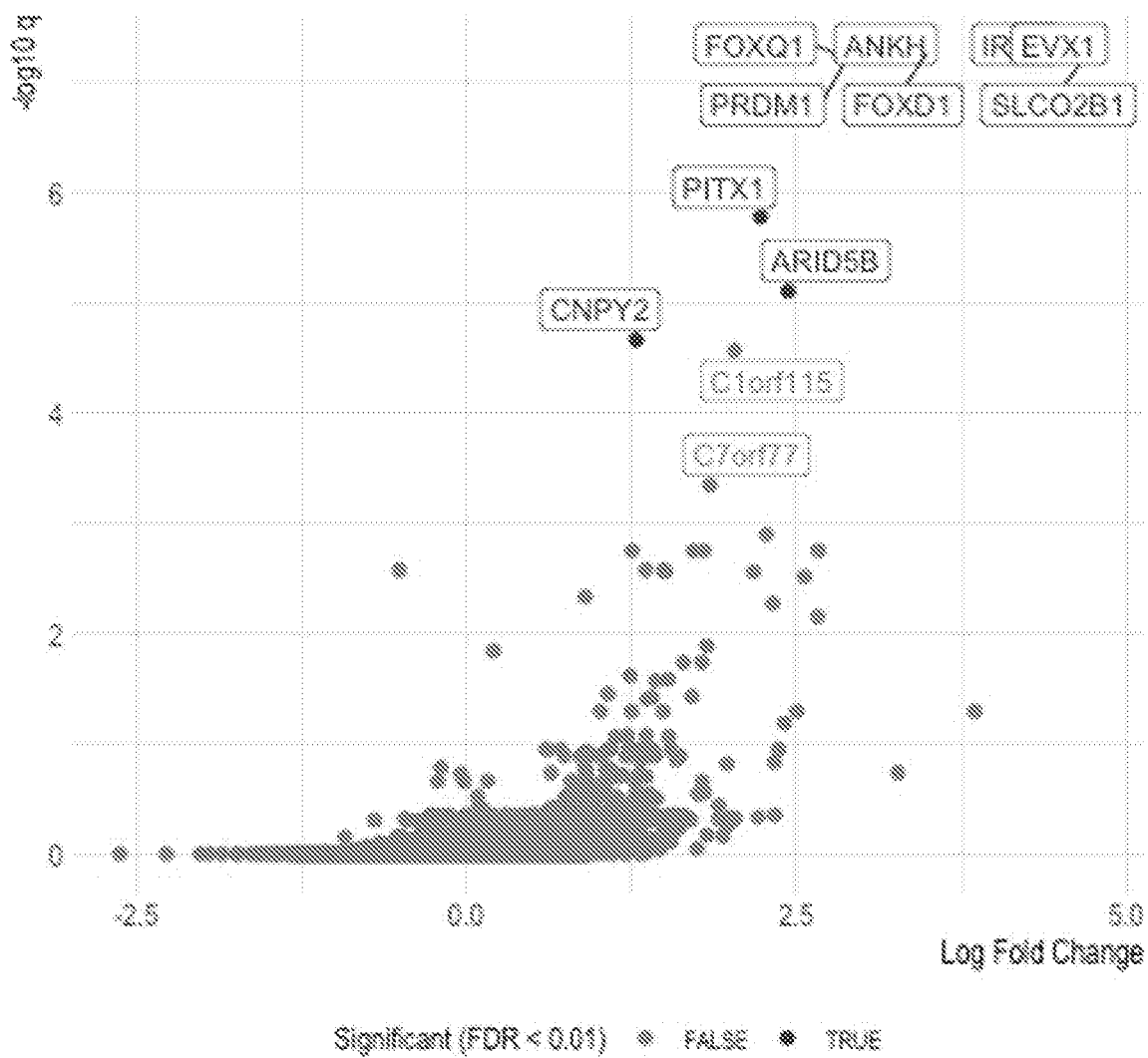

To identify potential mechanisms of acquired resistance to tepoxalin, an analogous genome-wide CRISPR activation screen was performed. A two plasmid system encoding dCas9-VP64, a modified tracrRNA containing 2 MS2 loops and two pP7 loops, and a PP7-P65-HSF fusion protein was employed. LS1034 cells stably expressing dCas9 were infected with the Calabrese guide library set B targeting 18,843 genes with 56,476 gRNAs. Following selection, cells were cultured in 8 or 16 μM of tepoxalin for 2 weeks before genomic DNA was harvested and sequenced. The top depleted gene in the screen related to DMSO was ABCB1, indicating that increased expression of the same target sensitized cells to tepoxalin (FIG. 5A). Thus, tepoxalin sensitization was strikingly enhanced by overexpression of ABCB1. Genes found to confer resistance included multiple developmental transcriptional modulators including EVX1, FOXDI, and FOXQ1 (FIG. 5B).

Figure 6B:
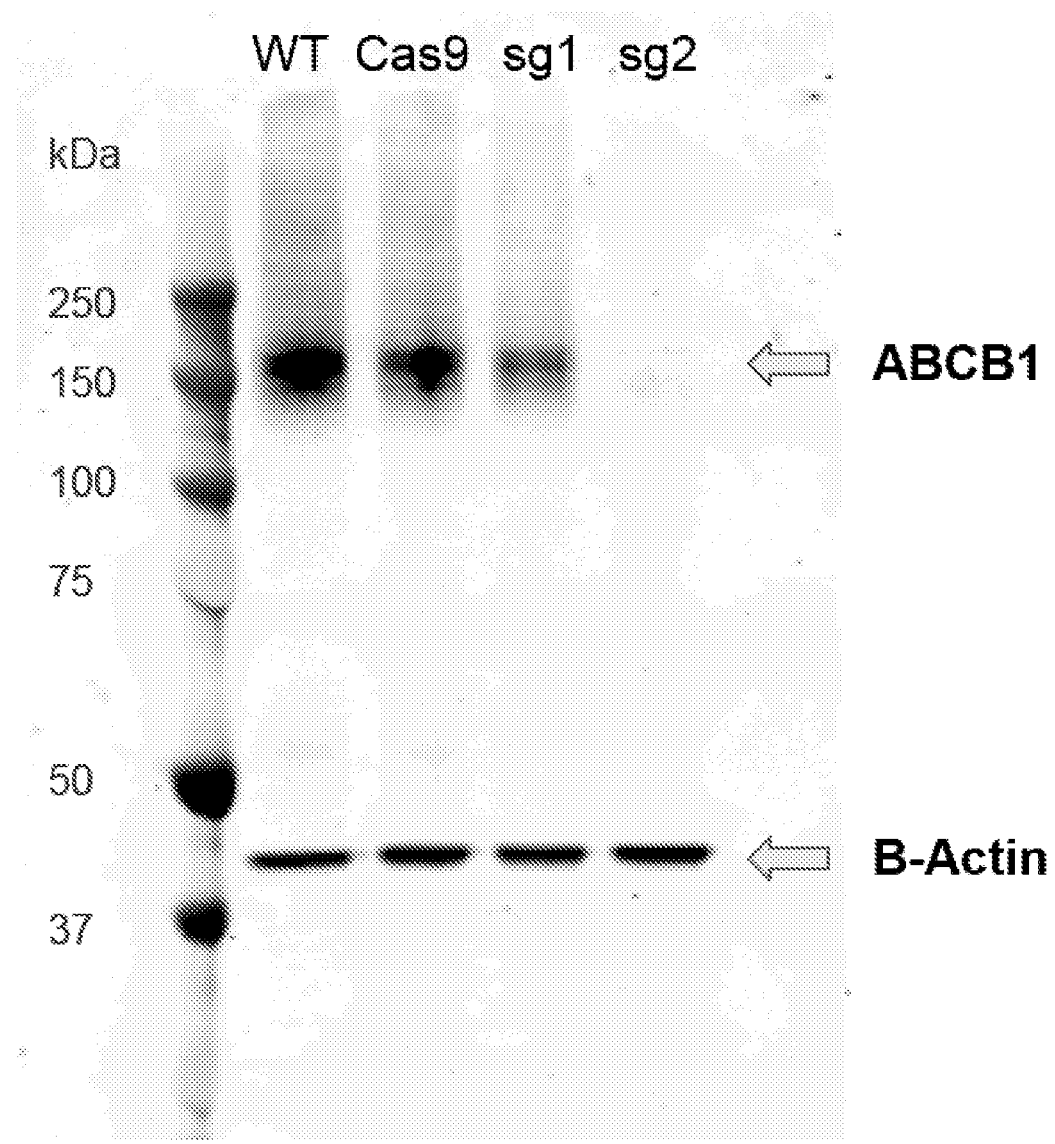
Figure 6C:
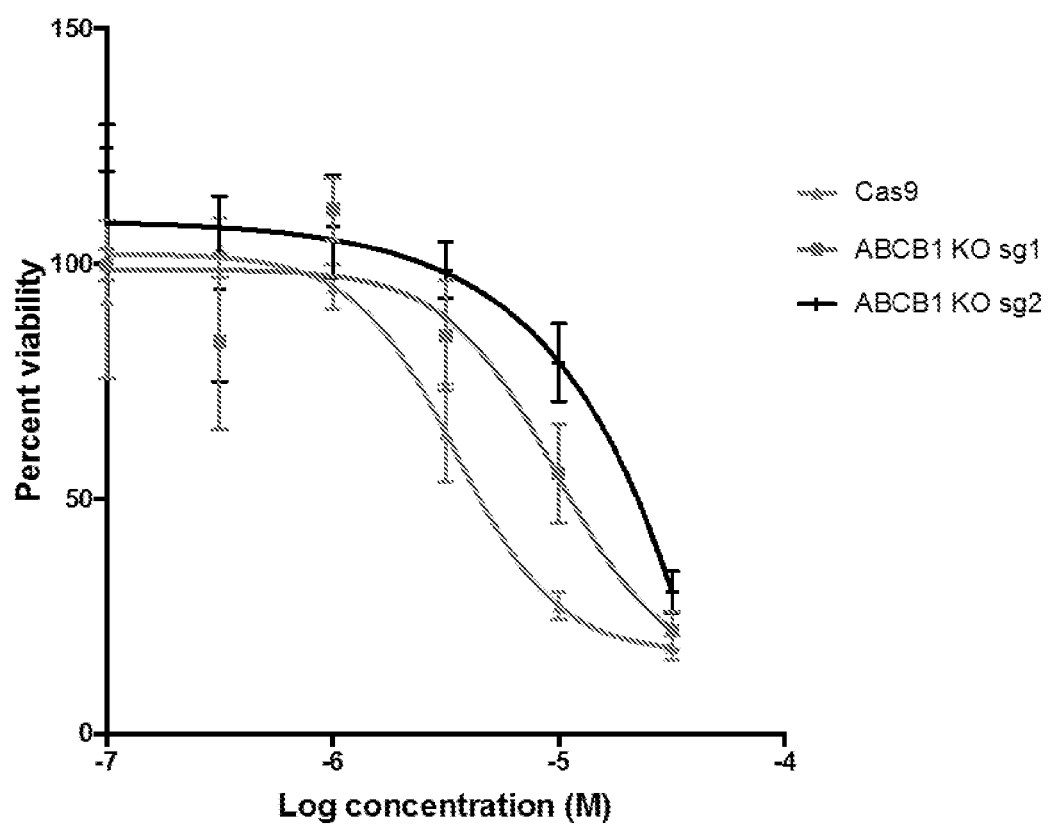

In the CRISPR modifier screen, certain sgRNAs targeting ABCB1 possessed greater knockdown efficacy than others. In particular, a tested "sg1" agent was observed to produce a 51% indel frequency when ABCB1 genomic DNA (gDNA) indel formation was assessed, whereas a tested "sg2" agent was observed to produce a 90% indel frequency in the same assessment (FIG. 6A). The observed variation between "sg1" and "sg2" agents was further observed to translate into varying levels of ABCB1 knockout: the "sg2" agent knocked down ABCB1 protein levels in LS1034 colon cancer cells demonstrably more than "sg1" agent-mediated levels of ABCB1 protein knockdown; FIG. 6B). These increasing levels of observed ABCB1 knockdown identified for the "sg2" agent relative to the "sg1" agent were further observed to be protective of the tepoxalin-mediated killing effect in proportion to these respective agents' extent of ABCB1 knockdown, with the "sg2" agent observed to cause the greatest ABCB1 knockdown and also impart the greatest protection (partial rescue) against tapoxalin-mediated killing of assayed LS1024 cells at 72 hours post-administration (FIG. 6C), while the "sg1" agent produced only modest ABCB1 knockdown and also imparted only modest protection against tapoxalin-mediated killing in the assayed LS1024 cells.

Figure 7A:
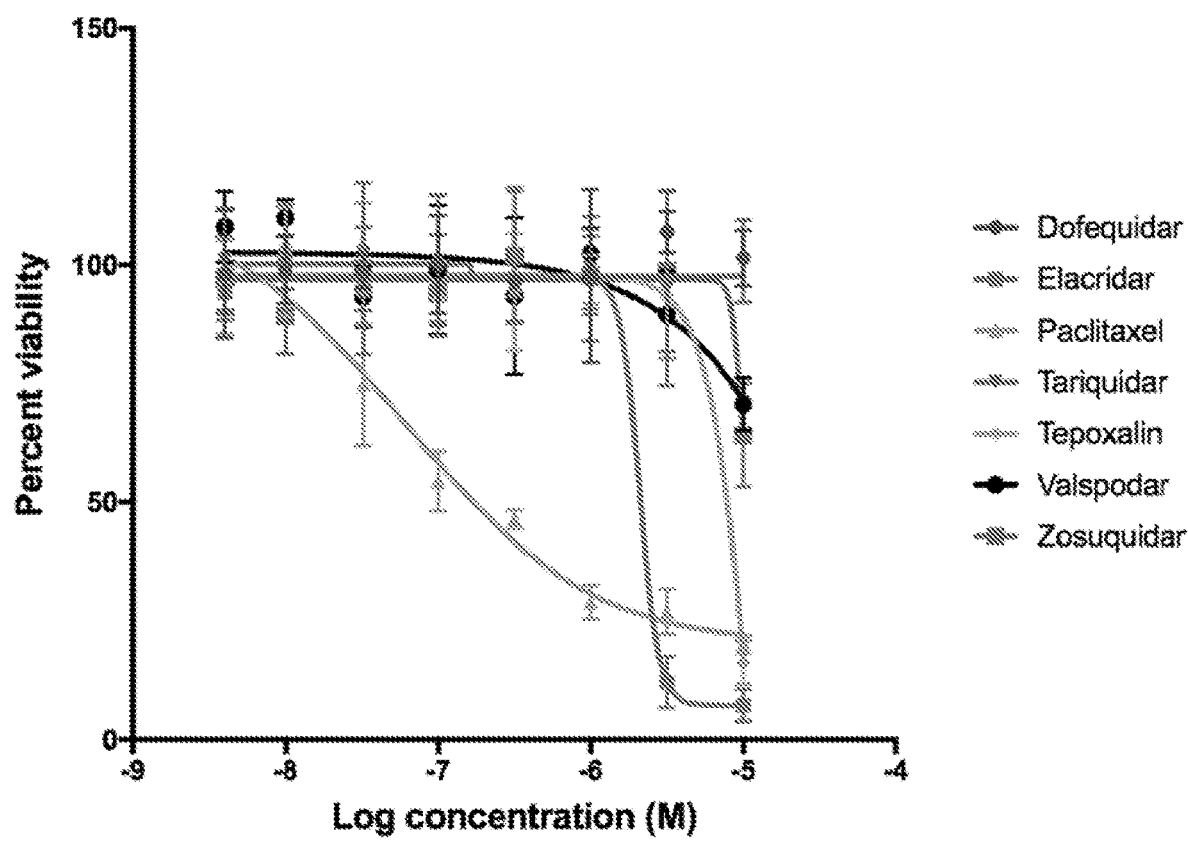

Assessment of the IC50 values for various chemotherapeutic agents and the p-glycoprotein (MDR1/ABCB1) inhibitor elacridar in killing LS1034 cells revealed an IC50 value (absolute) of 7.8 µM for tepoxalin, which was less robust than observed for paclitaxel (165 nM IC50) and elacridar (1.9 µM IC50), yet more robust than any of valspodar, zosuquidar, tariquidar or dofequidar (all having IC50 values >10 µM) (FIGS. 7A and 7B). Further to this initial IC50 assessment, an expanded IC50 assessment was performed to assess chemotherapeutic agent-mediated killing not only of LS1034, but also REC1 (a human B cell lymphoma cell line) and LS1034 administered either a control sgRNA (sg GFP) or an ABCB1-targeting knockdown sgRNA (sg ABCB1-2). Each of paclitaxel, tepoxalin, valspodar and zosuquidar exhibited more robust killing of REC1 cells than LS1034 cells, while elacridar exhibited comparable IC50 values for REC1 killing and LS1034 killing (FIG. 8). Consistent with the above-observed role of ABCB1 knockdown in rescue of tepoxalin-mediated cell killing, administration of sg ABCB1-2 to LS1034 cells effectively blocked tepoxalin-mediated cell killing, as compared to control sgRNA sg GFP. This result was unique to tepoxalin amongst the seven chemotherapeutic agents tested (FIG. 8).

Figure 9A:
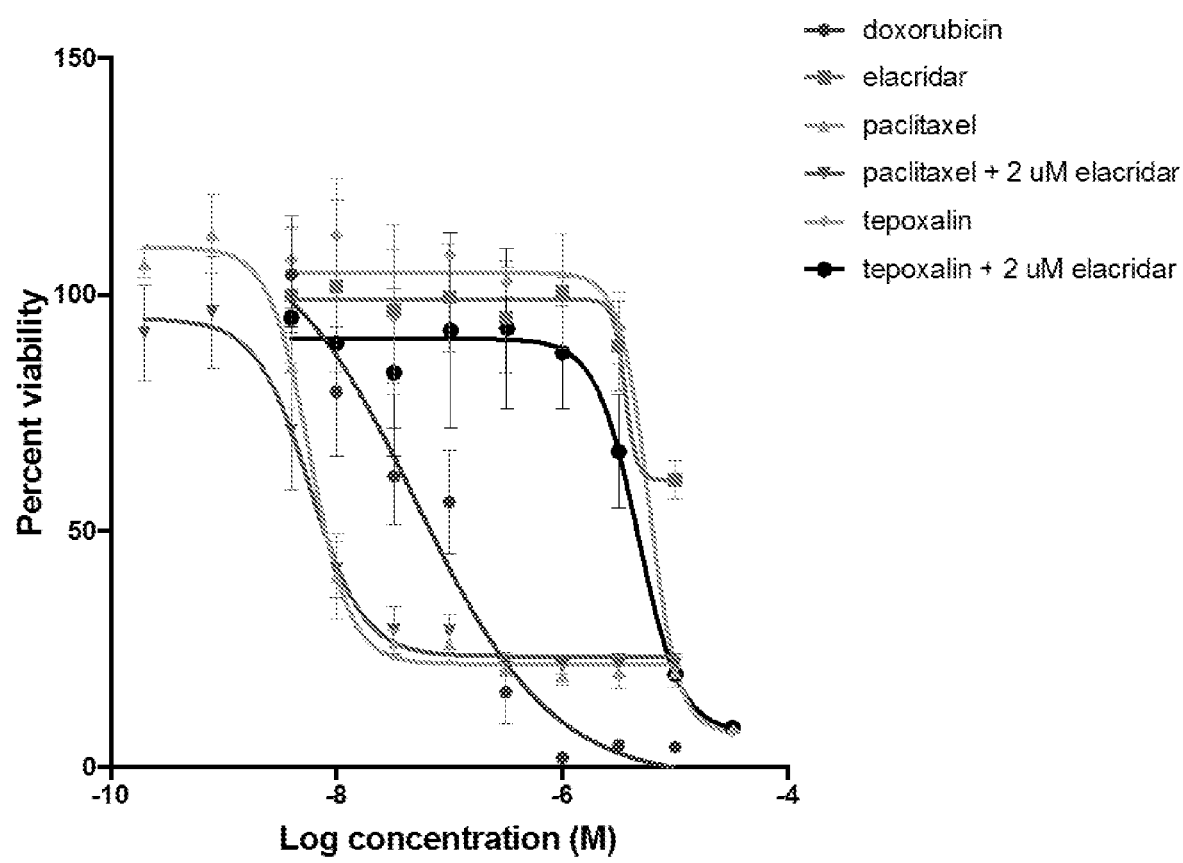
FIGS. 9A and 9B demonstrate that ABCB1 overexpression sensitized Kuramochi cells to tepoxalin.
Figure 9B:
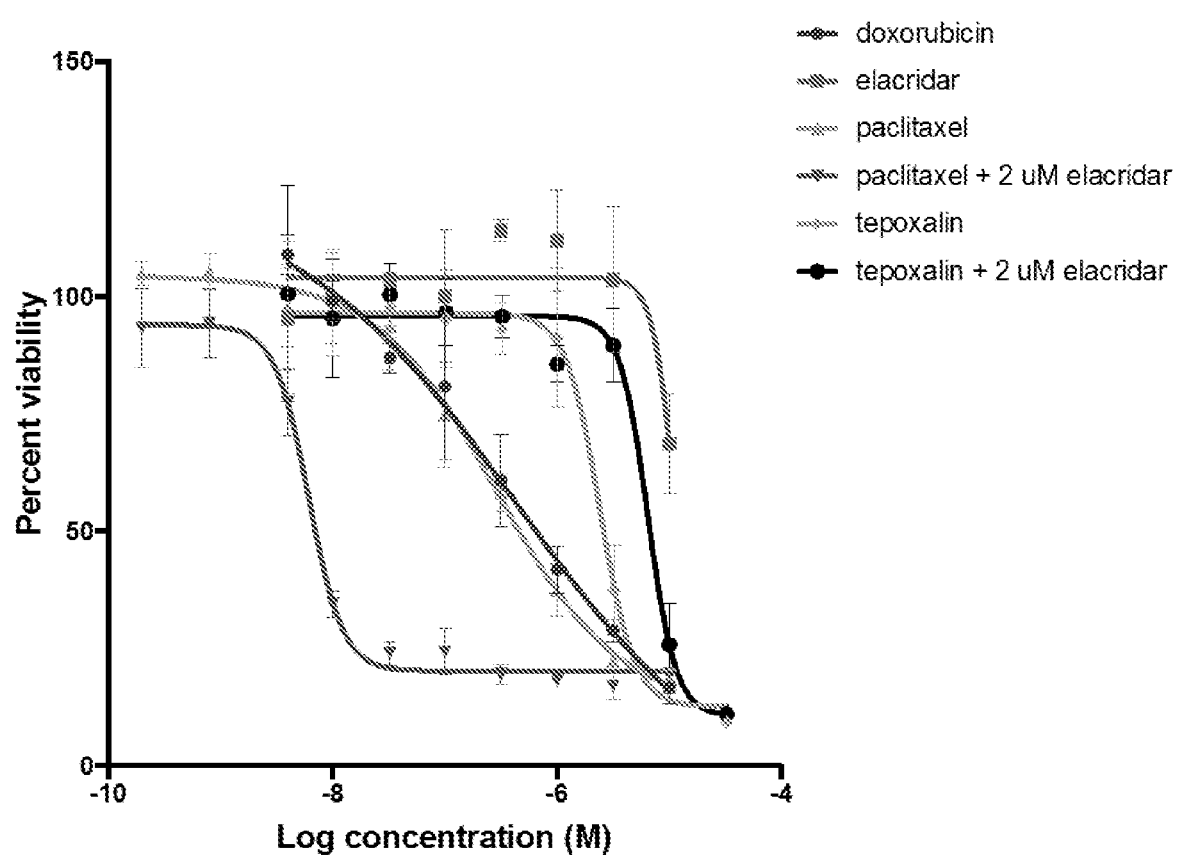

Next, the consequence of ectopic ABCB1 overexpression in cells resistant to tepoxalin was evaluated. Kuramochi, a cell line with low endogenous ABCB1 expression, was sensitized to tepoxalin while becoming more resistant to paclitaxel following introduction of an ABCB1 transgene (FIGS. 9A and 9B). This effect was reversible upon co-treatment with elacridar, an ABCB1 small molecule inhibitor, indicating that functional activity of the protein was required. Specifically, assessment of IC50 values performed upon transgenic Kuramochi cell lines that overexpressed ABCB1 revealed a tepoxalin-sensitizing effect of ABCB1 overexpression, consistent with the one initially identified above. Chemotherapeutic agent-mediated killing of native Kuramochi cells or transgenic Kuramochi cells overexpressing ABCB1 ("Kuramochi-ABCB1") was assessed at 144 hours. Both paclitaxel-mediated killing and doxorubicin-mediated killing was observed to be dampened in the presence of overexpressed ABCB1, as compared to such killing absent ABCB1 overexpression (compare FIG. 9A (low ABCB1 expression) with FIG. 9B (ABCB1 overexpressing)). In particular, rightward shifts in both paclitaxel and doxorubicin dose-response curves were observed in moving from native Kuramochi cells (FIG. 9A) to transgenic Kuramochi cells that overexpressed ABCB1 (FIG. 9B), demonstrating that ABCB1 overexpression blocked both paclitaxel-mediated killing and doxorubicin-mediated killing (thereby leading to higher IC50 values) of Kuramochi cells. In contrast, tepoxalin-mediated cell killing of Kuramochi cells was enhanced (the tepoxalin curve moved leftward) in moving from native Kuramochi cells (FIG. 9A) to transgenic Kuramochi cells that overexpressed ABCB1 (FIG. 9B). Interestingly, while the MDR1 (ABCB1) inhibitor elacridar alone exhibited only modest cell killing in both native Kuramochi cells (FIG. 9A) and in transgenic Kuramochi cells that overexpressed ABCB1 (FIG. 9B), combination administration of either paclitaxel with 2 µM elacridar or tepoxalin with 2 µM elacridar resulted in dose-response cell killing curves that were impervious (did not shift) to varying levels of ABCB1 expression/overexpression, again consistent with the necessary activity of ABCB1 in the cell killing effects observed.

To more fully investigate the mechanism of the ABCB1 knockout and overexpression effects that were observed, both a monolayer transport assay and a calcein AM assay, as each described in Filaria J. (2003 Oct. 24; 2 Suppl 1: S8), were employed. In a monolayer transport assay, tepoxalin was observed to have an IC50 of 12 µM, while verapamil exhibited an IC50 of 16 µM in the transport assay. In the calcein AM assay, which relies upon cell-permeability of compounds to observe an effect, tepoxalin was observed to have an IC50 of 32 µM, whereas the tepoxalin metabolite RWJ20142 was observed to have an IC50 value in excess of 100 µM.

Figure 10A:
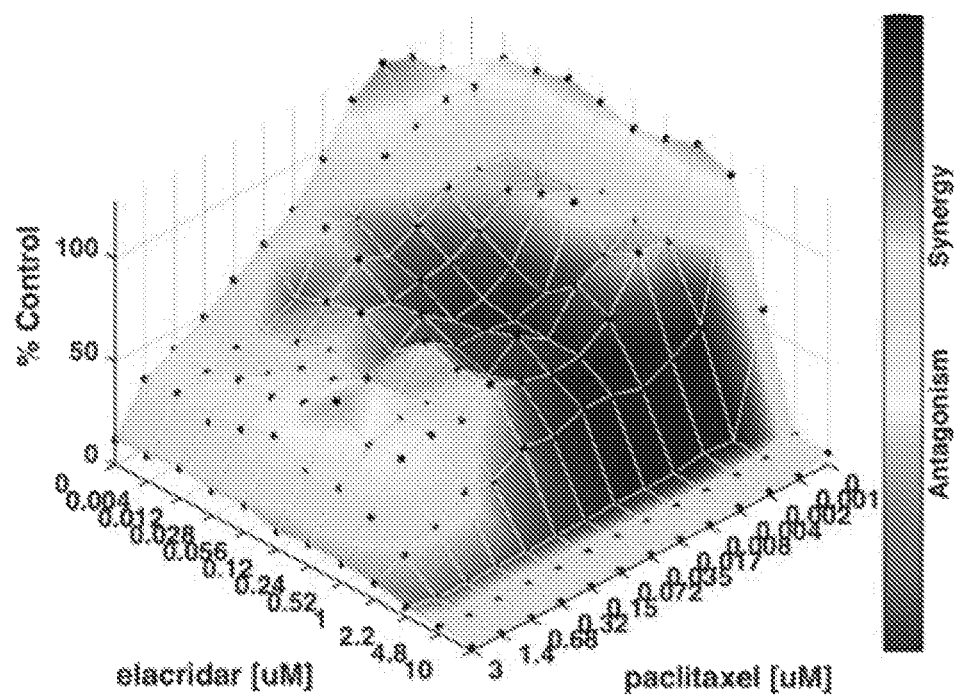
FIGS. 10A and 10B demonstrate that MDR1 inhibitor (elacridar) co-treatment sensitized cells to paclitaxel but rescued cells from tepoxalin-mediated cell killing.
Figure 10B:
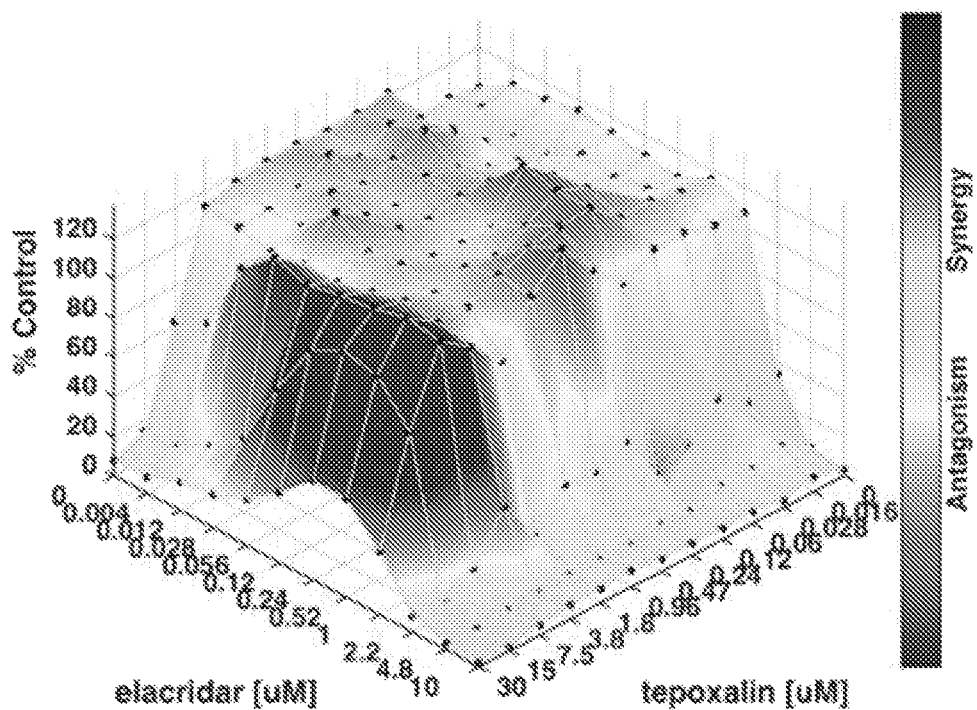

The extent of synergy between an MDR1 inhibitor, elacridar, and paclitaxel or tepoxalin, respectively, was examined across dose ranges for each drug. As shown in FIG. 10A, co-treatment of paclitaxel with elacridar sensitized treated LS1034 to paclitaxel. In contrast, co-treatment of tepoxalin with elacridar rescued tepoxalin-treated LS1034 cells from tepoxalin-mediated killing (FIG. 10B).

Figure 11:
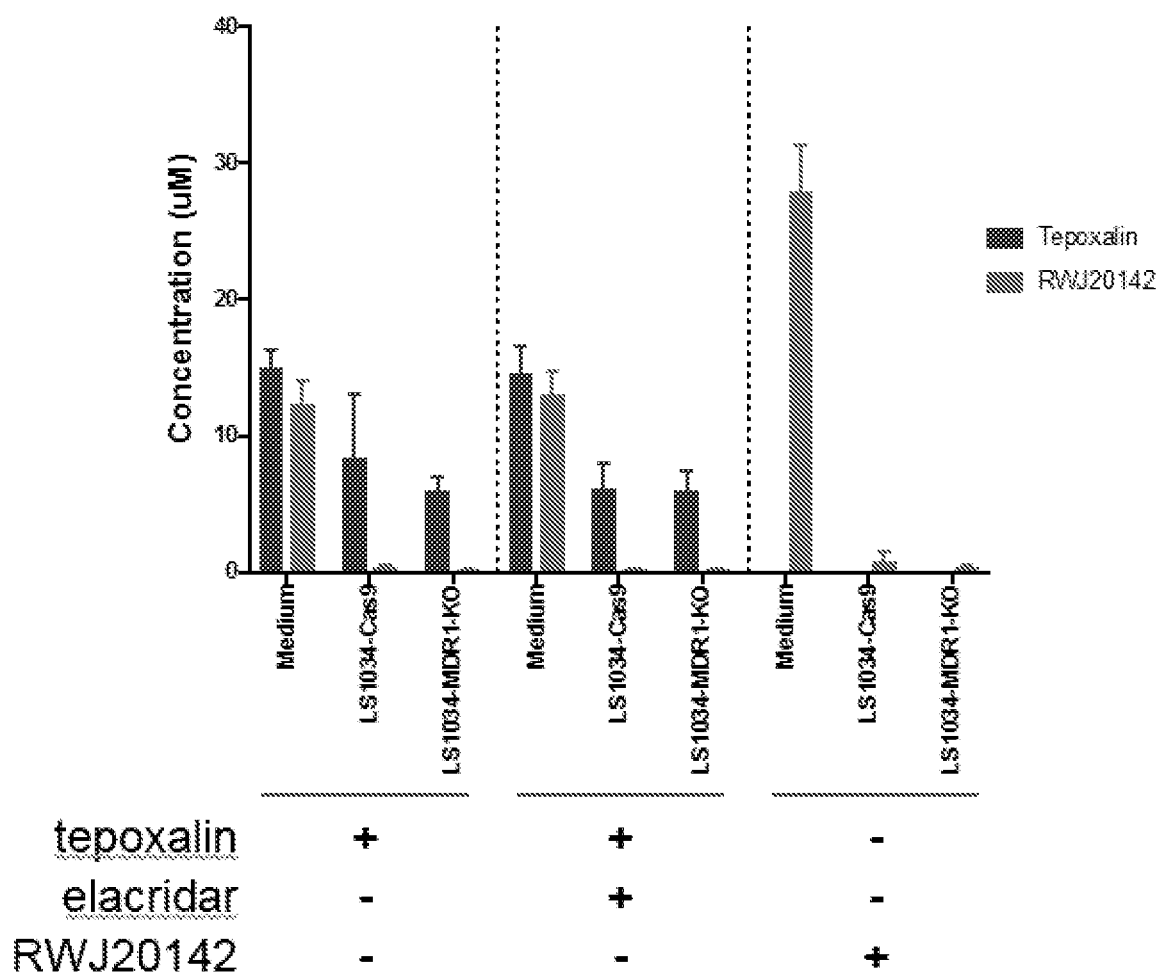
FIG. 11 shows that tepoxalin readily crossed the cell membrane (in LS1034 cells, with or without a MDR1 (ABCB1) knockout) but that the tepoxalin metabolite RWJ20142 was cell membrane-impermeable.

Tepoxalin has been previously described as metabolized in vivo to RWJ20142 following conversion of the hydroxamic acid to a carboxylic acid (3). RWJ20142 is an active metabolite that is active against cyclooygenase in vitro. Published pharmacokinetic studies have shown that RWJ20142 achieves a higher maximal plasma concentration than the parent compound. In order to test the metabolite, RWJ20142 was synthesized and its identity was confirmed by liquid chromatography-mass spectrometry. Unlike tepoxalin, RWJ20142-treated LS1034 cells showed no decrease in viability. Cellular permeability assays using LC-MS showed that tepoxalin, but not RWJ20142, was readily cell permeable in LS1034 cells (FIG. 11). Such results were consistent with the above-described calcein AM assay results for RWJ20142, whereas tepoxalin exhibited cell membrane permeability that was unaffected by the presence or absence of the MDR1 inhibitor elacridar (and therefore was an effect independent of the actions of the ABCB1/MDR1 pump)—thus, knockout of ABCB1 or co-treatment with elacridar did not alter compound permeability. In contrast, the tepoxalin metabolite RWJ20142 consistently demonstrated cell impermeability. Such permeability study assessments (with tepoxalin and RWJ20142 concentrations measured by mass spectrometry) were performed following a 3 hour incubation, with indicated drugs (tepoxalin, RWJ20142 and/or elacridar) administered at 20 µM concentration. Medium concentrations were compared to LS1034 concentrations, either in the presence or absence of an ABCB1 knockout.

Example 3: Therapeutic Testing of Tepoxalin

Tepoxalin's activity is tested in in vivo xenograft models, with the downstream mechanism for tepoxalin-induced cell death thereby further investigated. Derivatives of tepoxalin, as well as derivatives of the RWJ20142 tepoxalin metabolite, are also synthesized and tested for cell killing activity.

REFERENCES

1. Argentieri, D. C. et al. Tepoxalin: a dual cyclooxygenase/5-lipoxygenase inhibitor of arachidonic acid metabolism with potent anti-inflammatory activity and a favorable gastrointestinal profile. *J. PharmacoL Exp. Ther.* 271, 1399-1408 (1994).
2. Dubey, R. et a/. Chromatin-Remodeling Complex SWI/SNF Controls Multidrug Resistance by Transcriptionally Regulating the Drug Efflux Pump ABCB1. *Cancer Res.* 76, 5810-5821 (2016).
3. Waldman, S. A. et al. Pharmacokinetics and pharmacodynamics of tepoxalin after single oral dose administration to healthy volunteers. *J. Clin. PharmacoL* 36, 462-468 (1996).
4. Barretina, J. et al. The Cancer Cell Line Encyclopedia enables predictive modelling of anticancer drug sensitivity. *Nature* 483, 603-607 (2012).
5. Yu, C. et a/. High-throughput identification of genotype-specific cancer vulnerabilities in mixtures of barcoded tumor cell lines. *Nat. Biotechnol.* 34, 419-423 (2016).
6. Subramanian, A. et a/. A Next Generation Connectivity Map: L1000 Platform and the First 1,000,000 Profiles. *Cell* 171, 1437-1452.e17 (2017).
7. Zhang, X. D. A pair of new statistical parameters for quality control in RNA interference high-throughput screening assays. *Genomics* 89, 552-561 (2007).
8. Johnson, W. E., Li, C. & Rabinovic, A. Adjusting batch effects in microarray expression data using empirical Bayes methods. *Biostatistics* 8, 118-127 (2007).
9. Smirnov, P. et al. PharmacoGx: an R package for analysis of large pharmacogenomic datasets. *Bioinformatics* 32, 1244-1246 (2016).
10. Tsherniak, A. et al. Defining a Cancer Dependency Map. *Cell* 170, 564-576.e16 (2017).
11. Doench, J. G. et al. Optimized sgRNA design to maximize activity and minimize off-target effects of CRISPR-Cas9. *Nat. Biotechnot* 34, 184-191 (2016).

All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

One skilled in the art would readily appreciate that the present disclosure is well adapted to carry out the objects and obtain the ends and advantages mentioned, as well as those inherent therein. The methods and compositions described herein as presently representative of preferred embodiments are exemplary and are not intended as limitations on the scope of the disclosure. Changes therein and other uses will occur to those skilled in the art, which are encompassed within the spirit of the disclosure, are defined by the scope of the claims.

In addition, where features or aspects of the disclosure are described in terms of Markush groups or other grouping of alternatives, those skilled in the art will recognize that the disclosure is also thereby described in terms of any individual member or subgroup of members of the Markush group or other group.

The use of the terms "a" and "an" and "the" and similar referents in the context of describing the disclosure (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

Embodiments of this disclosure are described herein, including the best mode known to the inventors for carrying out the disclosed invention. Variations of those embodiments may become apparent to those of ordinary skill in the art upon reading the foregoing description.

The disclosure illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present disclosure provides preferred embodiments, optional features, modification and variation of the concepts herein disclosed may be resorted to by those skilled in the art, and that such modifications and variations are considered to be within the scope of this disclosure as defined by the description and the appended claims.

It will be readily apparent to one skilled in the art that varying substitutions and modifications can be made to the invention disclosed herein without departing from the scope and spirit of the invention. Thus, such additional embodiments are within the scope of the present disclosure and the following claims. The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context. Those skilled in the art will recognize, or be able to ascertain using no more than routine experimentation, many equivalents to the specific embodiments of the disclosure described herein. Such equivalents are intended to be encompassed by the following claims.

We claim:

1. A method for treating a subject having cancer, the method comprising:
   (a) identifying the presence in a sample of the subject of one or more of the following: (i) high ABCB1 mRNA expression levels, (ii) high ABCB1 protein expression levels and/or (iii) amplification of the ABCB1 locus, in the sample as compared to an appropriate control level; and
   (b) administering tepoxalin to the subject; thereby treating the subject having cancer.

2. The method of claim 1, wherein the cancer is selected from the group consisting of lung, colorectal, kidney, hepatic, lymphoma, bone, ovarian, biliary tract and thyroid cancer.

3. The method of claim 1, wherein step (a) comprises identifying the presence in the sample of elevated ABCB1 mRNA expression, as compared to an appropriate control.

4. The method of claim 1, wherein identifying step (a) comprises use of a kit for identifying high expression of ABCB1 mRNA or protein in a sample, as compared to an appropriate control level, consisting essentially of an oligonucleotide for detection of ABCB1 mRNA or an anti-ABCB1 antibody, and instructions for its use.

5. The method of claim 1, wherein the subject is human.

6. The method of claim 1, wherein the cancer is resistant to a non-tepoxalin chemotherapeutic drug.

7. The method of claim 1, wherein the appropriate control level is a level that is obtained from a normal, untreated, or control sample or cell population.

8. The method of claim 6, wherein the non-tepoxalin chemotherapeutic drug is selected from the group consisting of docetaxel, busulfan, carfilzomib, daunorubicin, doxorubicin, epirubicin, idarubicin, ixabepilone, paclitaxel, romidepsin, vincristine and vinorelbine.

9. A method for treating cancer in a subject, comprising:
   (a) identifying the presence in a sample of the subject of one or more of the following: (i) high ABCB1 mRNA expression levels, (ii) high ABCB1 protein expression levels and/or (iii) amplification of the ABCB1 locus, as compared to an appropriate control level; and
   (b) administering tepoxalin and a pharmaceutically acceptable carrier to the subject,
   thereby treating cancer in the subject.

10. The method of claim 9, wherein the cancer is selected from the group consisting of lung, colorectal, kidney, hepatic, lymphoma, bone, ovarian, biliary tract and thyroid cancer.

11. The method of claim 9, further comprising administering a non-tepoxalin chemotherapeutic drug to the subject.

12. The method of claim 11, wherein the non-tepoxalin chemotherapeutic drug is selected from the group consisting of docetaxel, busulfan, carfilzomib, daunorubicin, doxorubicin, epirubicin, idarubicin, ixabepilone, paclitaxel, romidepsin, vincristine and vinorelbine.

13. A method for treating cancer in a subject, the method comprising co-administering to a subject having a cancer possessing one or more of the following: (i) high ABCB1 mRNA expression levels, (ii) high ABCB1 protein expression levels and/or (iii) amplification of the ABCB1 locus, as compared to an appropriate control level, (a) tepoxalin and (b) a non-tepoxalin chemotherapeutic drug, thereby treating cancer in the subject.

14. The method of claim 13, wherein the cancer is selected from the group consisting of lung, colorectal, kidney, hepatic, lymphoma, bone, ovarian, biliary tract and thyroid cancer.

15. The method of claim 13, wherein the non-tepoxalin chemotherapeutic drug is selected from the group consisting of docetaxel, busulfan, carfilzomib, daunorubicin, doxorubicin, epirubicin, idarubicin, ixabepilone, paclitaxel, romidepsin, vincristine and vinorelbine.

* * * * *